Figure 4A:
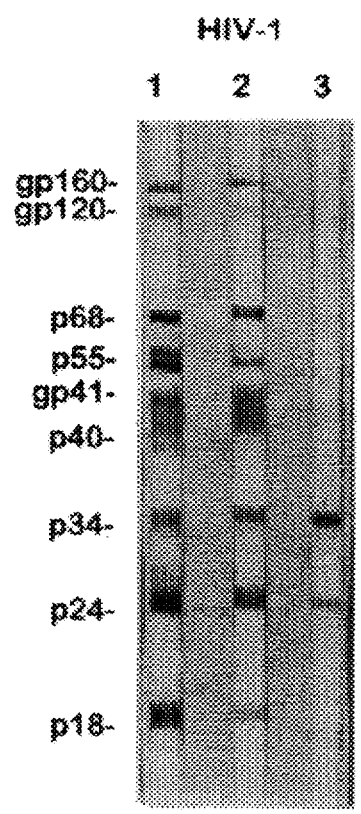

United States Patent [19]

De Leys et al.

[11] Patent Number: 5,795,743
[45] Date of Patent: Aug. 18, 1998

[54] HIV-3 RETROVIRUS ANTIGEN COMPOSITIONS

[75] Inventors: Robert De Leys, Grimbergen; Bart Vanderborght, Geel; Eric Saman, St. Niklaas; Hugo Van Heuverswyn, Laarne, all of Belgium

[73] Assignee: Innogenetics N.V., Ghent, Belgium

[21] Appl. No.: 486,836

[22] Filed: Jun. 7, 1995

Related U.S. Application Data

[62] Division of Ser. No. 228,519, Apr. 15, 1994, Pat. No. 5,567,603, which is a division of Ser. No. 460,913, filed as PCT/EP89/00643, Jun. 8, 1989, Pat. No. 5,304,466.

[30] Foreign Application Priority Data

Jun. 9, 1988 [EP] European Pat. Off. .............. 88109200

[51] Int. Cl.$^6$ .............. C12P 21/00; C12Q 1/70; C12N 7/01; C12N 7/02
[52] U.S. Cl. .............. 435/69.3; 435/5; 435/7; 435/235; 530/320.1; 530/350
[58] Field of Search .............. 435/5, 7, 235, 435/69.3; 530/320.1, 350

[56] References Cited

U.S. PATENT DOCUMENTS 4,839,288  6/1989  Montagnier .............. 435/235

FOREIGN PATENT DOCUMENTS 239425   9/1987  European Pat. Off. .
86/02383 4/1986  WIPO .

OTHER PUBLICATIONS

Rayfield et al., *Emerging Infectious Diseases* 2:209–212 (1996).
Janssens et al., *AIDS* 8:1012–1013 (1994).
Simon et al., *AIDS* 8;1628–1629 (1994).
Gürtler et al., *Journal of Virology* 68:1581–1585 (1994).
Vanden Haesevelde et al., *Journal of Virology* 68:1586–1596 (1994).

Franchini, et al., AIDS Research and Human Retroviruses, vol. 23, No. 1, 1987, "Genetic Analysis of a New Subgroup of Human and Simian T–lymphotropic Retroviruses: HTLV–IV, LAV–2, SBL–6669, and STLV–III$_{AGM}$", pp. 11–17.

Clavel et al., Science, vol. 233, Jul. 18, 1986, "Isolation of a New Human Retrovirus from West Africa Patients with AIDS", pp. 343–346.

Clavel et al., Nature, vol. 324, No. 18, Dec. 25, 1986, "Molecular Cloning and Polymorphism of the Human Immune Deficiency Virus Type 2", pp. 691–695.

Guyader et al., Nature, vol. 326, Apr. 16, 1987, "Genome Organization and Transactivation of the Human Immunodeficiency Virus Type–2", pp. 662–669.

Hahn et al., Nature, vol. 330, Nov. 12, 1987, "Relation of HTLV–4 to Simian and Human Immunodeficiency–associated viruses", pp. 184–186.

Fukasawa et al., Nature, vol. 333, No. 6172, Jun. 2, 1988, "Sequence of Simian Immunodeficiency Virus From Africa Green Monkey, a New Member of the HIV/SIV Group", pp. 457–461.

*Primary Examiner*—Michael P. Woodward
*Assistant Examiner*—Mary K. Zeman
*Attorney, Agent, or Firm*—Arnold, White & Durkee

[57] ABSTRACT

Described is a new variety of retrovirus designated HIV-3 samples of which are deposited in the European Collection of Animal Cell Cultures (ECACC) under V88060301. Further described are antigens obtained from the virus, particularly proteins p12, p16, p25 and glycoproteins gp41 and gp120 to be used in the diagnosis of ARC or AIDS caused by HIV-3. Immunogenic compositions to be used as vaccines contain an envelope glycoprotein of HIV-3 such as gp41 or gp120.

12 Claims, 16 Drawing Sheets

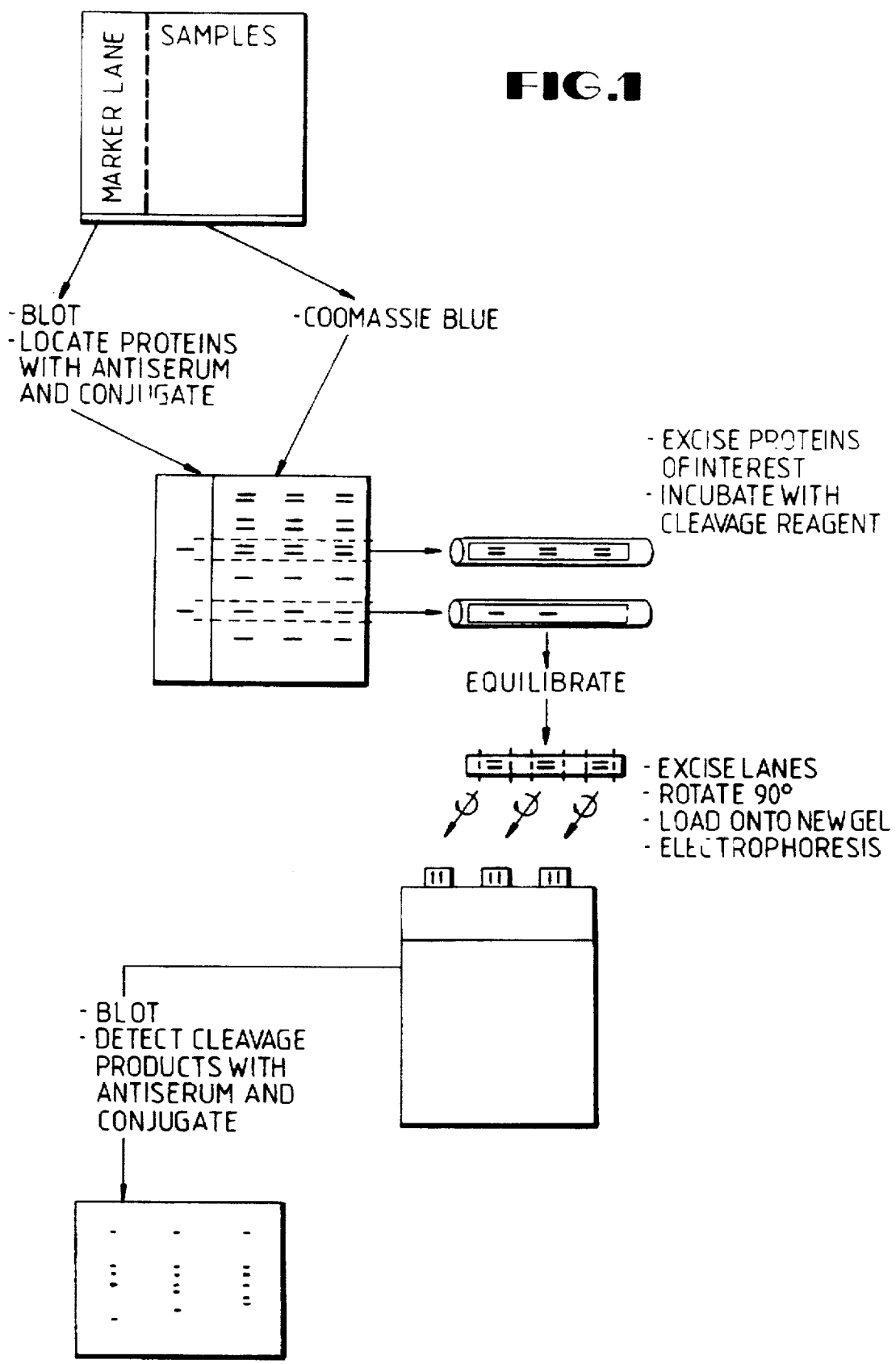

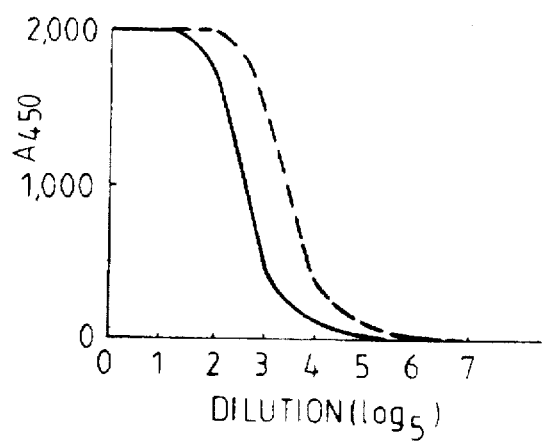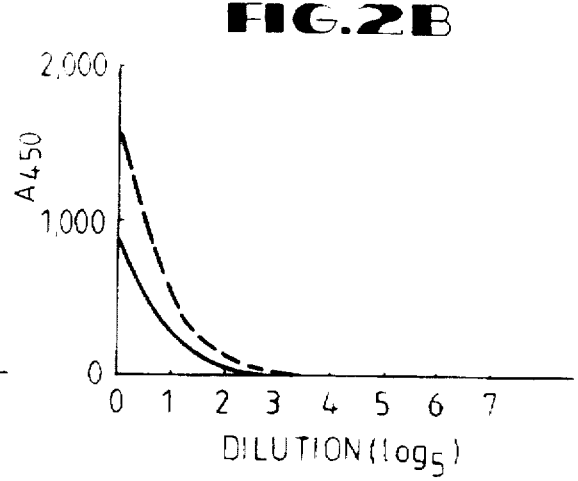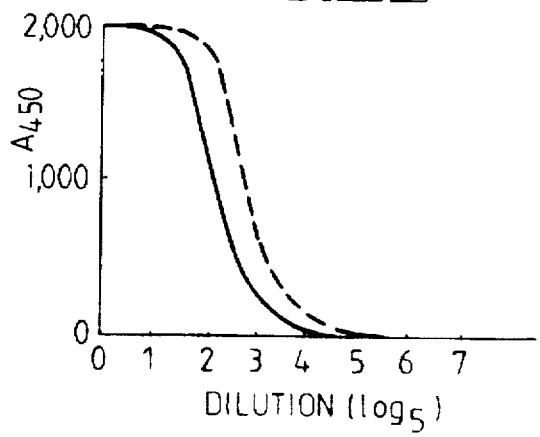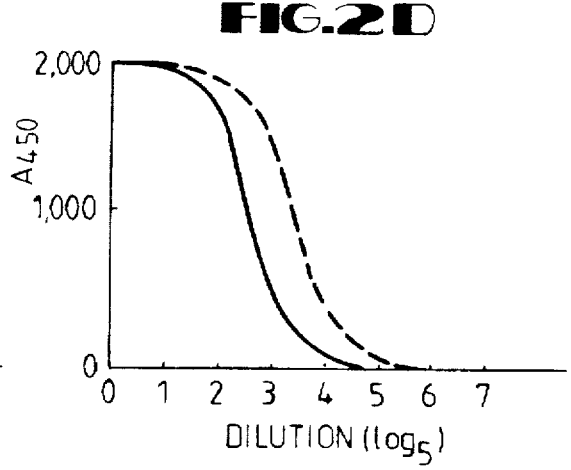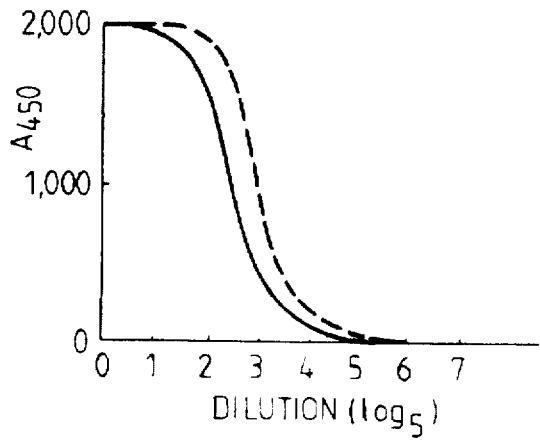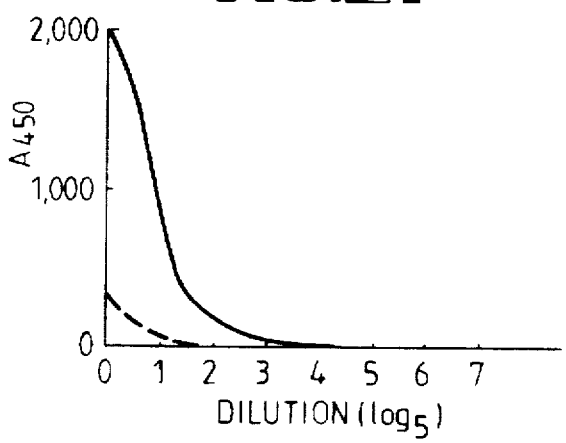

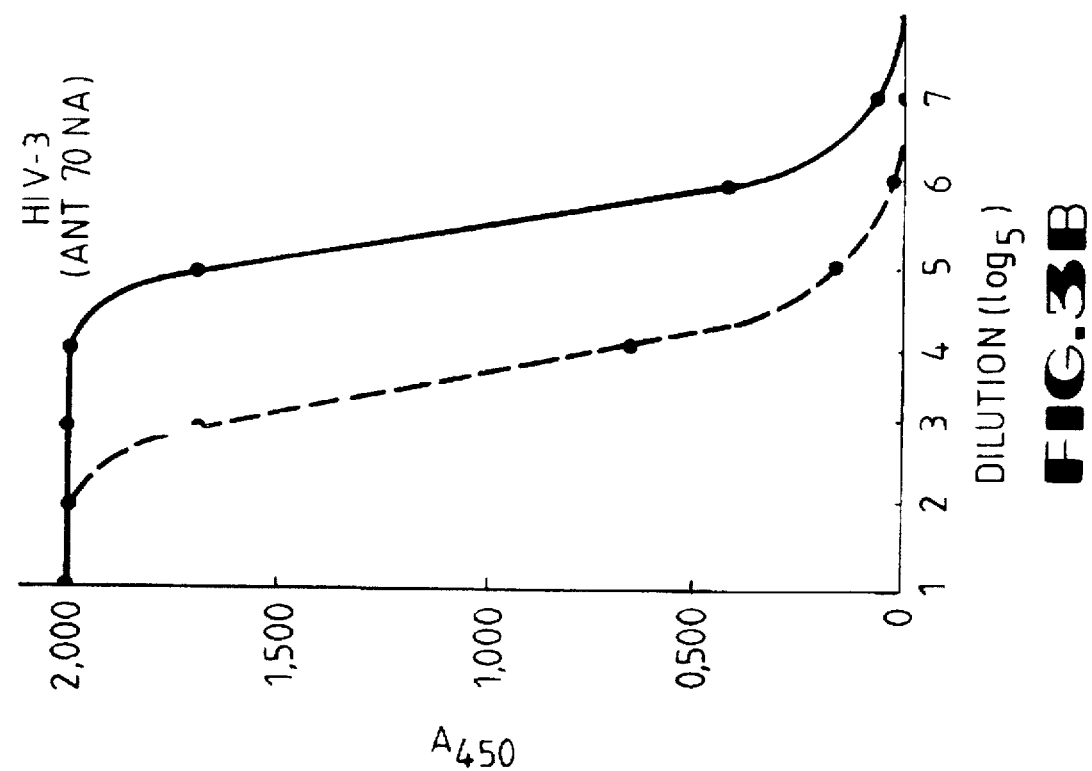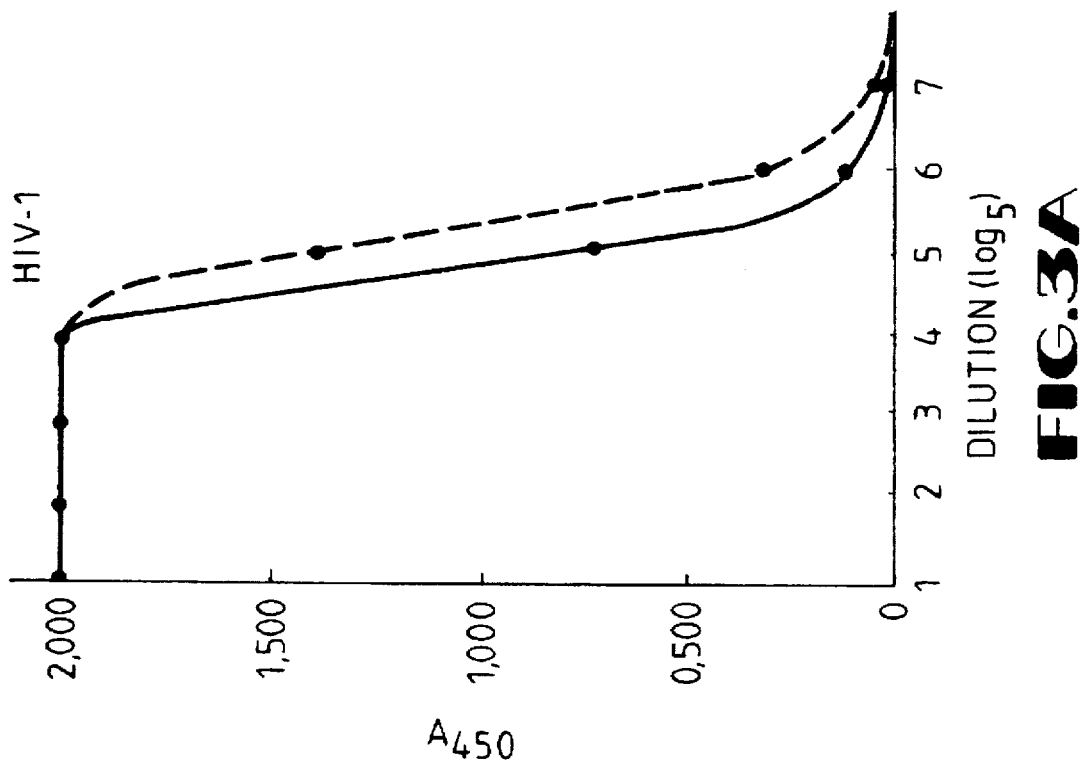

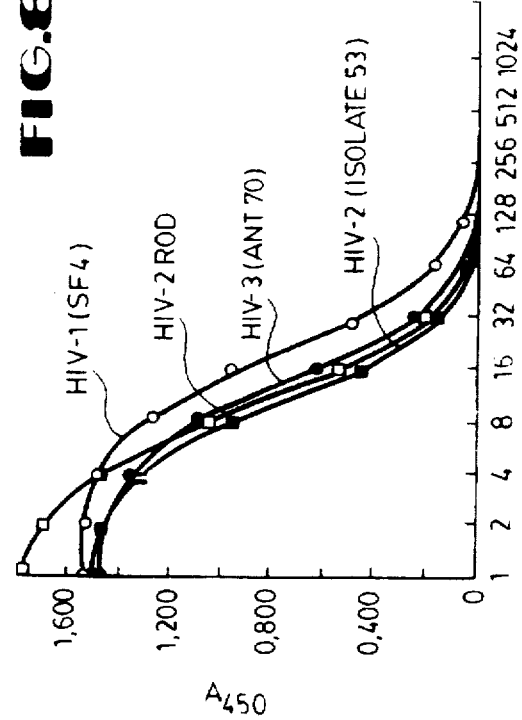
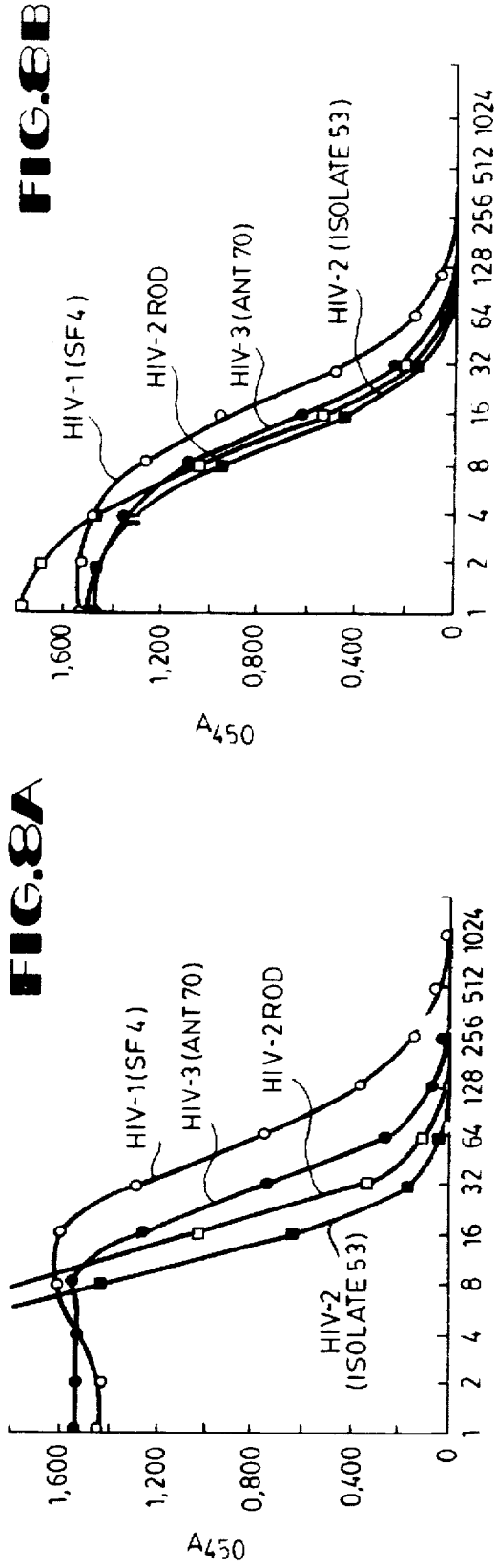
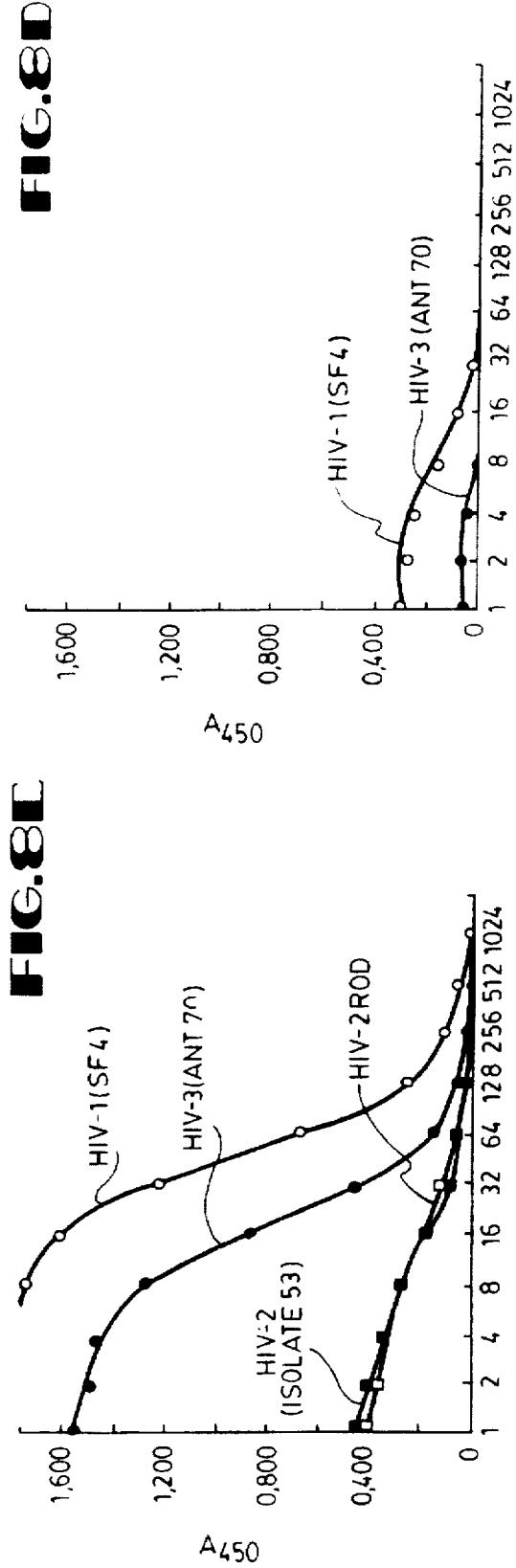

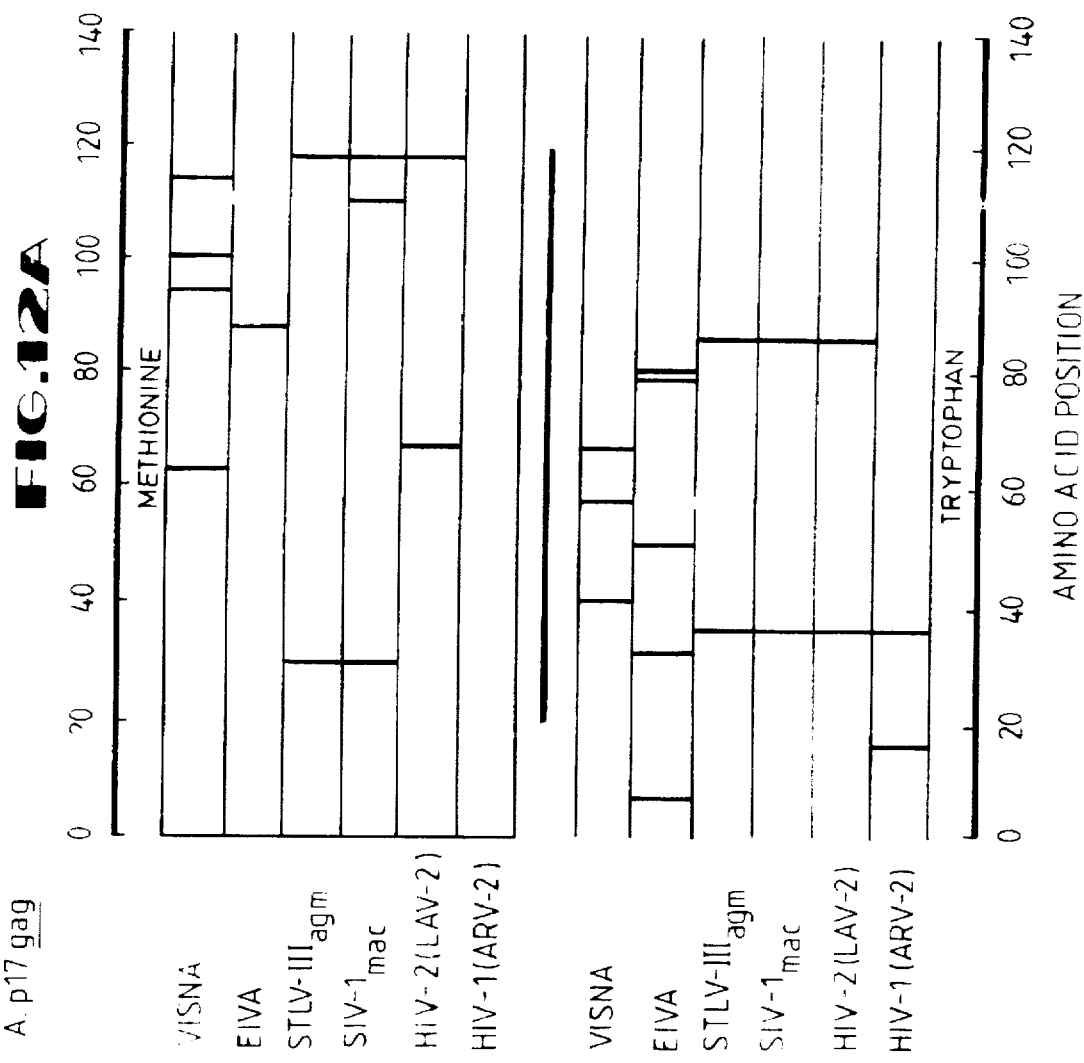

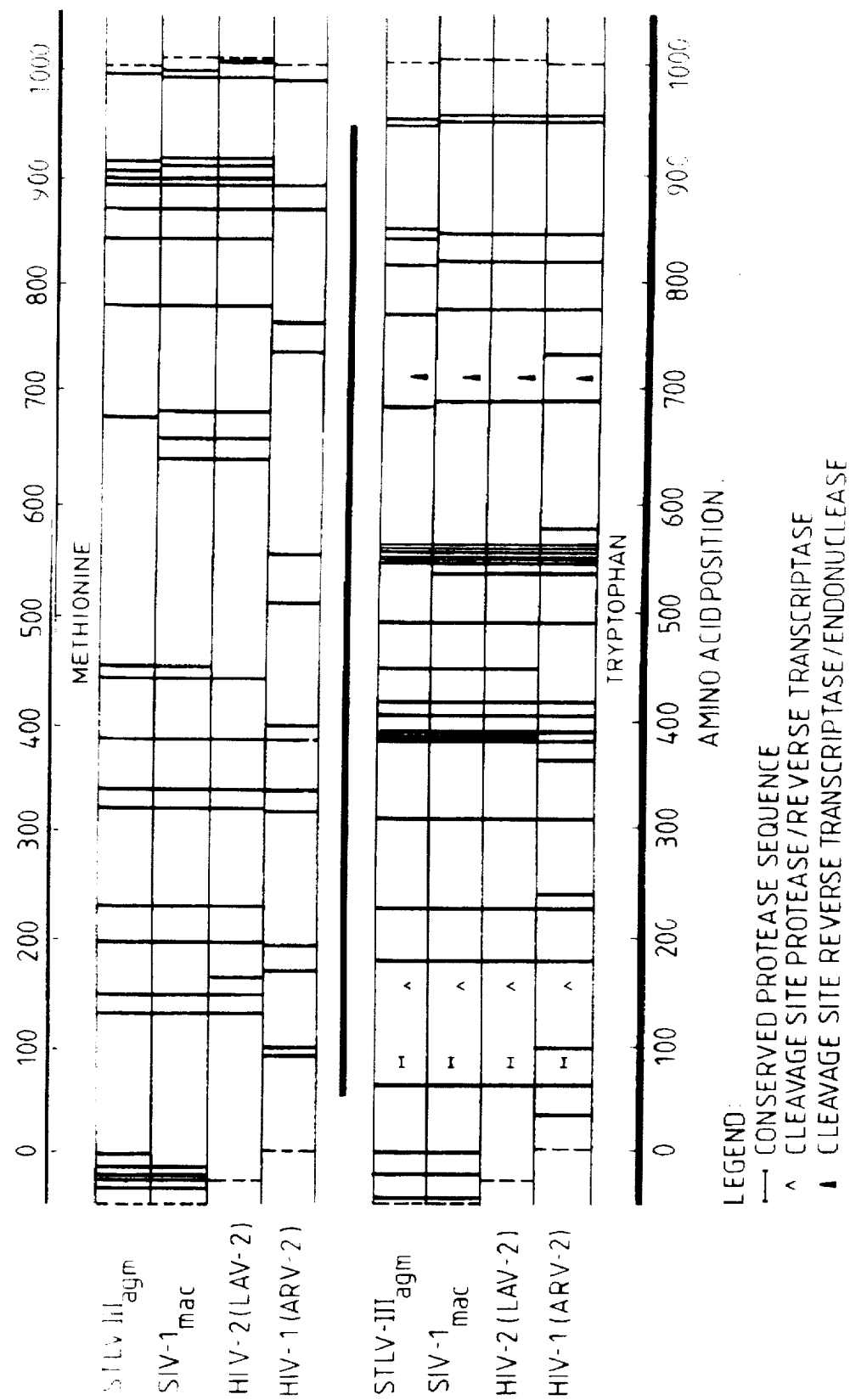

FIG. 14A-I
STRINGENT
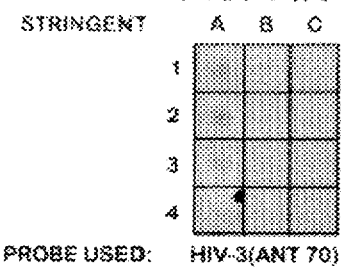
PROBE USED: HIV-3(ANT 70)
FIG. 14A-II
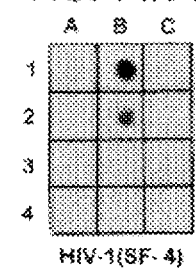
HIV-1(SF-4)
FIG. 14A-III
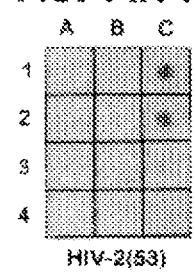
HIV-2(53)
FIG. 14B-I
NONSTRINGENT
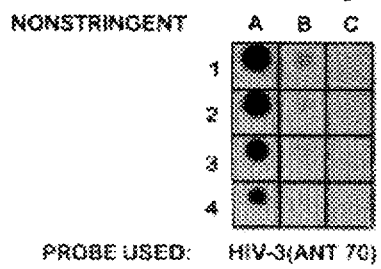
PROBE USED: HIV-3(ANT 70)
FIG. 14B-II
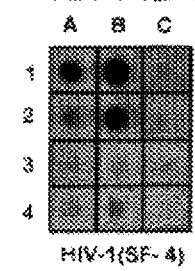
HIV-1(SF-4)
FIG. 14B-III
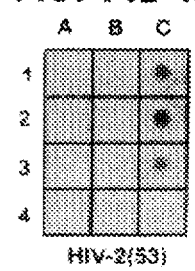
HIV-2(53)
LEGEND:
VIRUS SPOTTED:
A HIV-3(ANT 70)
B HIV-1(SF-4)
C HIV-2(ISOLATE 53)
ML. EQUIVALENT CULTURE SUPERNATANT:
1. 5 ml.
2. 2.5 ml.
3. 1.3 ml.
4. 0.6 ml.

HIV-3 RETROVIRUS ANTIGEN COMPOSITIONS

This application is a divisional of pending application Ser. No. 08/228,519, filed Apr. 15, 1994 which is a divisional of application Ser. No. 07/460,913, filed Mar. 23, 1990, issued as U.S. Pat. No. 5,304,466 on Apr. 19, 1994, which claims benefit under 35 U.S.C. § 120 of PCT/EP89/00643 filed Jun. 8, 1989 and claims priority under 35 U.S.C. § 119 of EP 88 109 200.1 filed Jun. 9, 1988.

Substantial progress has been made in our understanding of the acquired immunodeficiency syndrome or AIDS. The prinicipal causative agent has been demonstrated to be a non-transforming retrovirus with a tropism for T4 helper/inducer lymphocytes (1,2) and it has been estimated that millions of people world-wide have already been infected. Infection with this virus leads, at least in a significant percentage of cases, to a progressive depletion of the T4 lymphocyte population with a concomittant increasing susceptibility to the opportunistic infections which are characteristic of the disease. Epidemiological studies indicate that human immunodeficiency virus type 1 (HIV-1), the etiological agent responsible for the majority of AIDS cases and which is currently the most widely disseminated HIV, probably had its origins in Central Africa (3). The discovery of this virus did not necessarily imply the existence of other types of human immunodeficiency viruses. Nevertheless, a second group of human immunodeficiency-associated retroviruses, human immunodeficiency virus type 2 (HIV-2),was identified in West Africa (4,5). An HIV-2 virus is disclosed in EP-A-0 239 425. An HIV-1 virus is disclosed in WO 86/02383. Other similar, but not identical, retroviruses have also been isolated from simian sources (simian immunodeficiency virus, SIV) such as African green monkeys (6,7) and macaques (8,9). The simian isolates have been shown to be genetically more closely related to HIV-2 than HIV-1 but are nevertheless distinct (10).

One characteristic of human immunodeficiency viruses which complicates their comparison is their genetic variability; genetic variants arise spontaneously and with high frequency. A comparison of various HIV-1 isolates revealed that some regions of the genome are highly variable while others are reasonably well conserved (11–16). Similar polymorphisms have also been observed for HIV-2 (17). The regions with the greatest genetic stability are presumably those regions coding for the regions of viral proteins which are structurally or enzymatically essential. The viral genes with the greatest overall genetic stability are the gag and pol genes, while some regions of the env gene and the genes coding for regulatory proteins such as art, tat, sor and 3' orf exhibit a high degree of variability. Some of the major structural features of the gag and pol gene products are apparently shared not only by all of the variants of a particular HIV type, but have, at least to some extent, been conserved between virus types. Antiserum produced against HIV-1 crossreacts with the gag and pol gene products of HIV-2, albeit with a lower affinity than for the corresponding HIV-1 gene products. However, in spite of the demonstrable immunological crossreaction, at the nucleic acid level there is little sequence homology and no significant hybridization between these two viruses can be detected except under very low stringency conditions (17).

A higher degree of relatedness can be demonstrated between SIVagm (STLV-III agm, nearly or completely identical to Human Lymphotropic Virus type 4 (15)) and HIV-2. Immunological crossreaction is not limited only to the gag and pol gene products but extends to the env gene products as well. Nevertheless, genomic analysis of SIVagm and HIV-2 showed them to be genetically distinguishable (19). DNA probes specific for HIV-2, although able to hybridize to SIVagm sequences, hybridize preferentially to HIV-2 (18).

We now report the isolation and characterization of a novel human immunodeficiency virus from a Camerounian woman and her partner. Geographically, this virus comes from a region in Africa located between West Africa where HIV-2 is endemic, and East-Central Africa where HIV-1 is endemic. This isolate is shown immunologically to be antigenically more closely related to HIV-1 than is HIV-2, yet an analysis of partial cleavage products obtained by chemical cleavage of the gag and pol gene products demonstrate that this isolate is neither HIV-1 nor HIV-2. This novel isolate could represent an evolutionary link between HIV-1 and HIV-2. This novel virus will be referred to as HIV-3 hereinafter.

Subsequent to the filing of this application, the medical industry and scientific community has recognized the change in classification of HIV-3 to HIV-1 subtype 0. See, e.g., Rayfield et al., *Emerging Infectious Diseases* 2:209–212 (1996); Janssens et al., *AIDS* 8:1012–1013 (1994); Simon et al., *AIDS* 8:1628–1629 (1994); Gurtler et al., *Journal of Virology* 68:1581–1585 (1994); and Vanden Haesevelde et al., *Journal of Virology* 68:1586–1596 (1994).

Accordingly, the invention relates to an HIV-3 retrovirus or variants of this virus having the essential morphological and immunological properties of the retrovirus deposited in the European Collection of Animal Cell Cultures (ECACC) under V 88060301.

A virus isolation was performed from blood from an asymptomatic Camerounian woman who is the partner of an HIV-seropositive man with generalized lymphadenopathy. Serum from the woman was moderately positive (ratio O.D./cut-off of 4.5) in the enzyme- linked immunosorbent assay (EIA, Organon Teknika) and had a low titer ($^1/_{40}$) in the immunofluorescent antibody assay for HIV-1 but gave ambiguous results in the HIV-1 Western blot assay with clear bands at p33, P53/55 and p64 but very weak bands at p24, gp41 and gp120. The virus was isolated by co-cultivation of the woman's lymphocytes with PHA-stimulated lymphocytes from healthy uninfected donors in a medium consisting of RPMI 1640 buffered with 20 mM HEPES (hydroxyethylpiperazine ethanesulfonate) and supplemented with 15% fetal calf serum, 5 g/ml hydrocortisone, 75 u/ml interleukin-2 (IL-2) and 2 g/ml polybrene.

After 52 days in culture, virus was detected in the culture as judged by the presence of syncytia and on the basis of positive immunofluorescence observed when a laboratory reference anti-HIV antiserum was incubated with acetone-fixed cells from the culture. The presence of reverse transcriptase was also detected in the culture supernatant ($10^4$ cpm/ml, 27×background). Cell-free culture supernatant was used to passage the virus on fresh lymphocytes. After 15 days, CPE was again observed and reverse transcriptase detected in the supernatant. The virus was further propagated in PHA-stimulated lymphocytes from healthy blood donors and was transferred to continuous cell lines of leukemic origin. Virus-containing supernatant was tested in parallel with culture supernatants known to contain HIV-1 in the differential antigen capturing test which is described in detail below. The results of this comparison indicated that the new isolate was not HIV-1.

The new virus was then characterized with respect to its protein antigens and nucleic acids. The cell lines used for propagating the virus can be, depending on the case, lines of the CEM, HUT, Molt-4, or MT4 type, or any other immortalized cell line which bears the T4 receptor on its cell surface.

Figure 12B:
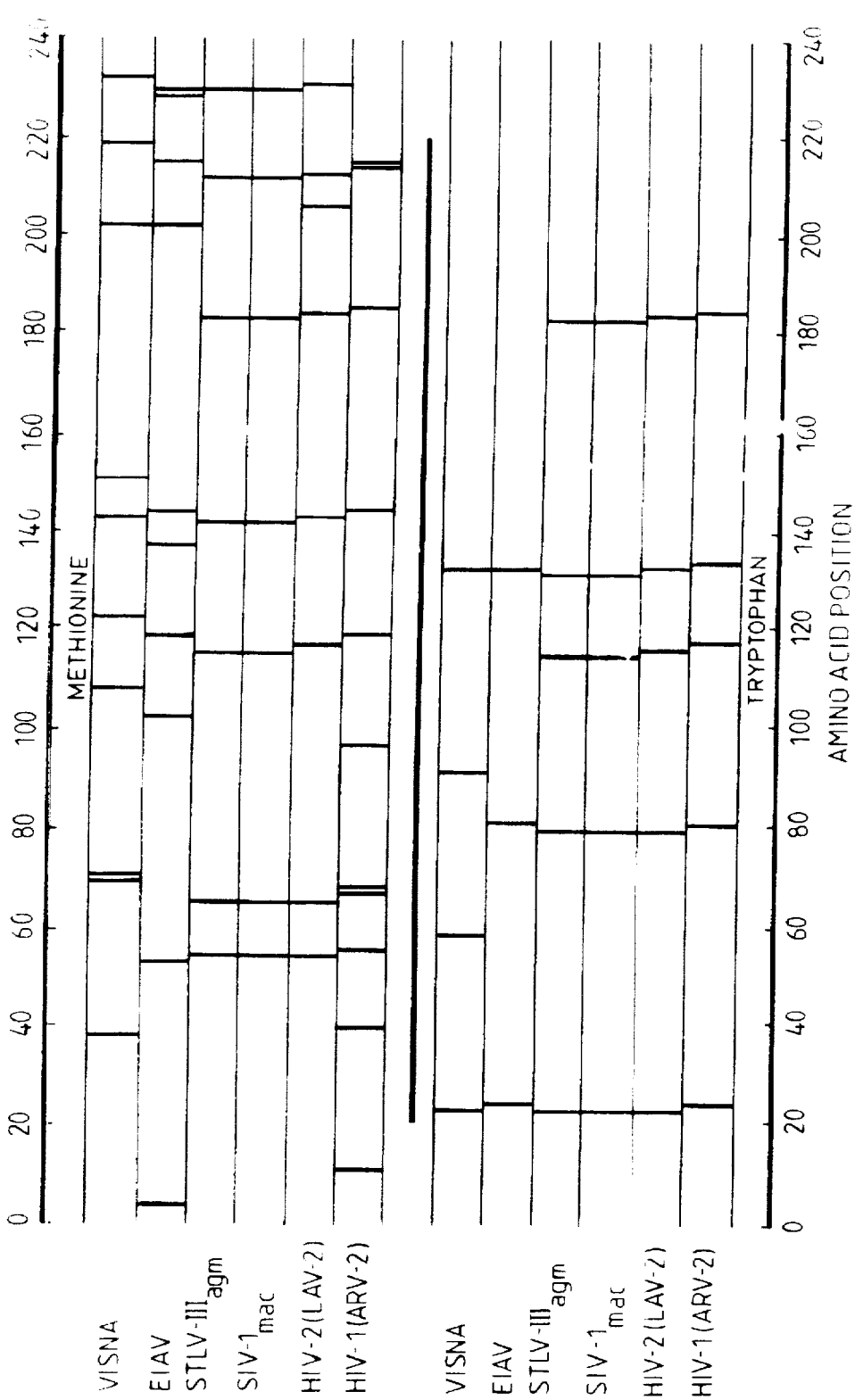

A preferred cell line for the continuous propagation of HIV-3 is Molt-4. Molt-4 cells infected with HIV-3 were deposited with the ECACC on Jun. 3, 1988 under number V 88060301. Establishment of a chronically-infected cell line can, for example, be carried out as follows:

Molt-4 cells (10^6/ml) and preferably Molt-4 clone 8 cells (obtained from N. Yamamoto, Yamaguchi, Japan) are cocultured with infected human lymphocytes (10^6/ml) in RPMI 1640 culture medium buffered with 20 mM HEPES and containing 10% fetal calf serum. Within one to two weeks, a cytopathic effect is observed in the culture which is followed by cell death. A fraction of the cells in the culture survive the infection and produce virus continuously. With continued culturing, these cells increase in number and can be passaged. Supernatants from these cells can be used a a source of virus.

Furthermore, the invention relates to a purified retrovirus having the essential morphological and immunological properties described below. In many cases, the unique characteristics of HIV-3 can best be appreciated by comparison with the same type of characteristics relating to the other human immunideficiency viruses, HIV-1 and HIV-2.

BRIEF DESCRIPTION OF THE DRAWINGS

In FIGS. 1 to 16 the designations HIV-3 (ANT 70) and HIV-3 (ANT 70 NA) refer to two strains of a new HIV-3 virus isolated from a Camerounian woman and her partner from which HIV-3 (ANT 70) has been deposited under ECACC V88060301.

FIG. 1 shows a procedure for preparing cleavage maps of viral proteins.

FIG. 2 shows differential antigen capturing on virus-containing culture supernatants.

Differential antigen capturing is performed as described hereinafter. The solid line represents the results obtained using a broad-spectrum anti-HIV-1 IgG while the broken line depicts the results obtained using an IgG which was rather specific for HIV-1. FIG. 2A, FIG. 2B, FIG. 2C, FIG. 2D, and FIG. 2E each shows a typical titration obtained with HIV-1. FIG. 2F shows the result obtained with HIV-3 (ANT 70) containing supernatant.

FIG. 3A shows differential antigen capturing on HIV-1 and FIG. 3B shows differential antigen capturing on HIV-3 (ANT 70NA) supernatants.

Differential antigen capturing was performed as described hereinafter. The solid line depicts the results obtained on plates coated with the broad spectrum anti-HIV IgG while the broken line represents the results obtained on plates coated with IgG which shows less crossreactivity with HIV types other then HIV-1.

FIG. 4A shows the reactivity of anti-HIV sera on HIV-1 and FIG. 4B shows the reactivity of anti-HIV sera on HIV-2 Western Blot strips.

The reactivities of 3 different sera on HIV-1 and HIV-2 Western blot strips are shown. Sera: 1. anti-HIV-1, 2. anti-HIV-3 (ANT 70), 3. anti-HIV-2 (isolate 53). The molecular weights indicated are those given by the manufacturer (Dupont Biotech).

FIG. 5 relates to the comparison of gag and pol proteins of several HIV-1 isolates, HIV-2rod and HIV-3 (ANT 70).

Proteins were separated electrophoretically and blotted as described later. The blot was incubated with a broad-spectrum anti-HIV antiserum followed by (anti-human IgG)/alkaline phosphatase-labeled conjugate to visualize the proteins. A. HIV-2rod, B. an HIV-1 laboratory isolate, C. HIV-3 (ANT 70), D. an HIV-1 laboratory isolate, E. HIV-1 (SF4).

FIG. 6 shows a comparison of HIV-3 (ANT 70) and HIV-3 (ANT 70 NA) proteins.

Proteins were separated electrophoretically and blotted as described later The blot was incubated with the BSR antiserum followed by (alkaline phosphatase)/anti-human IgG conjugate to visualize the proteins. Lane 1: HIV-3 (ANT 70 NA), lane 2: HIV-3 (ANT 70), lane 3: HIV-1 (SF4) . The apparent intensity difference between lanes 1 and 2 is caused by the difference in the amount of material loaded.

FIG. 7 relates to the ability of various human anti-HIV-1 sera to capture viral antigens.

A number of human sera were diluted 1:1000 and coated directly on microwell plates. Detergent-treated culture supernatants containing HIV-1 (SF4), HIV-3 (ANT 70), HIV-2rod or HIV-2 (isolate 53) were incubated and the bound antigen was detected using a broadspectrum (anti-HIV)/horseradish peroxidase conjugate. Sera 1-7 were of African origin while sera 8-11 were from Europeans. The greater ability of African sera to capture non-HIV-1 antigen can, in part, be explained by their higher anti-p24 titers (data not shown).

FIG. 8A, FIG. 8B, FIG. 8C, and FIG. 8D shows the effect of coating IgG dilution on the binding of HIV isolates.

Succesive 2-fold dilutions were made of four different sera, as shown in FIG. 8A, FIG. 8B, FIG. 8C, and FIG. 8D, beginning at a dilution of 1:1000 and were used to coat microwell plates. Detergent-treated supernatants of HIV-1 (SF4), HIV-3 (ANT 70), HIV-2rod and HIV-2 (isolate 53) were diluted to give approximately the same optical density on plates coated with the antiserum shown in panel B at a dilution of 1:1000. Bound antigen was detected using the broad-spectrum (anti-HIV IgG)/horseradish peroxidase conjugate.

FIG. 9 shows antigen capturing of virus isolates using human polyclonal and mouse anti-HIV-1 monoclonal antibodies.

Wells were coated and incubated as described in the text. The IgGs used are as follows:

1. human polyclonal anti-HIV IgG, 2. MAb CLB 59, 3. MAb CLB 21, 4. MAb CLB 64, 5. MAb CLB 14, 6. MAb CLB 16, 7. MAb CLB 47, 8. MAb CLB 13.6 (anti-p18), 9. MAb CLB 19.7, 10. Mab CLB 13.4 (anti-p18).

FIG. 10A, FIG. 10B, FIG. 10C, FIG. 10D, and FIG. 10E are a comparison of the reactivity of human anti-HIV antisera to different HIV types.

Lysates of HIV-1 (SF4), HIV-3 (ANT 70), HIV-2rod and HIV-2 (isolate 53) were separated electrophoretically on SDS-polyacrylamide gels, blotted onto nitrocellulose, and incubated with a high titer anti-HIV-1 antiserum (FIG. 10A), a lower titer anti-HIV-1 antiserum (FIG. 10B), serum from the woman from whom HIV-3 (ANT 70) was isolated (FIG. 10C), her partner from which HIV-3 (ANT 70 NA) was isolated (FIG. 10D) and anti-HIV-2 antiserum from the person from whom HIV-2 (isolate 53) was isolated (FIG. 10E).

FIG. 11A, FIG. 11B and FIG. 11C shows titrations of anti-HIV sera by enzyme immunoassay.

Microwell plates were coated with lysates of HIV-1 (SF4), HIV-3 (ANT 70) and HIV-2 (isolate 53). Serum from an HIV-1-infected European (FIG. 11A), antiserum to HIV-3 (ANT 70 NA) (FIG. 11B) and antiserum to HIV-2 (isolate 53) (FIG. 11C) were titrated in 2-fold dilutions beginning at a dilution of 1:100 on all three coated plates.

FIG. 12A, and FIG. 12B shows the positions of methionine and tryptophan residues in viral p17 and p24 gag gene products and FIG. 12C shows the position of methionine and tryptophan residues in viral pol gene products.

Amino acid positions for the p17 gag proteins are given starting from the first methionine in the coding sequence. Positions for the p24 gag protein are given starting at the p17/p24 proteolytic cleavage site. Positions for the pol gene are shown after alignment with the highly conserved tryptophan doublet in the HIV-1 sequence at positions 556 and 557. The positions of a conserved protease sequence, the protease/reverse transcriptase cleavage site and the reverse transcriptase/endonuclease cleavage site are indicated. In this case, the terms p24 and p17 are used in the genetic sense to refer to the largest and second largest viral core proteins respectively. The term "HIV-2 (LAV-2)" is a synonymum for HIV-2 rod.

Figure 13A:
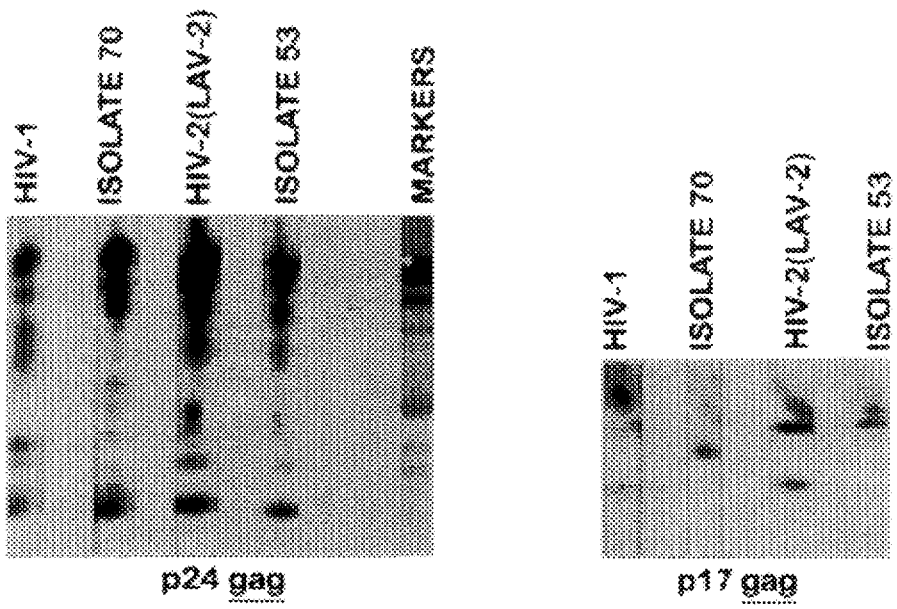
Figure 13B:
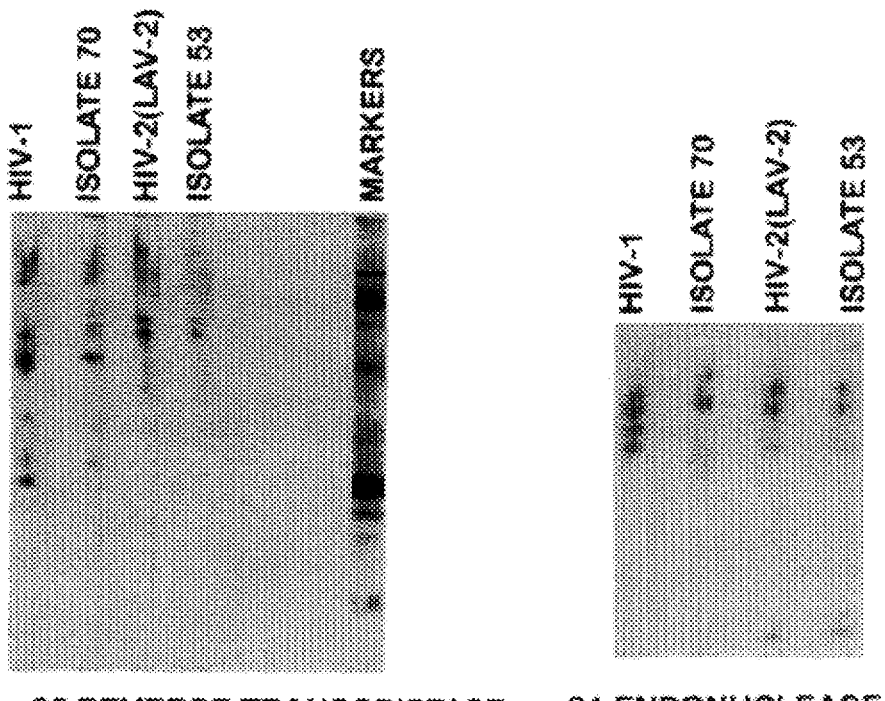
Figure 13C:
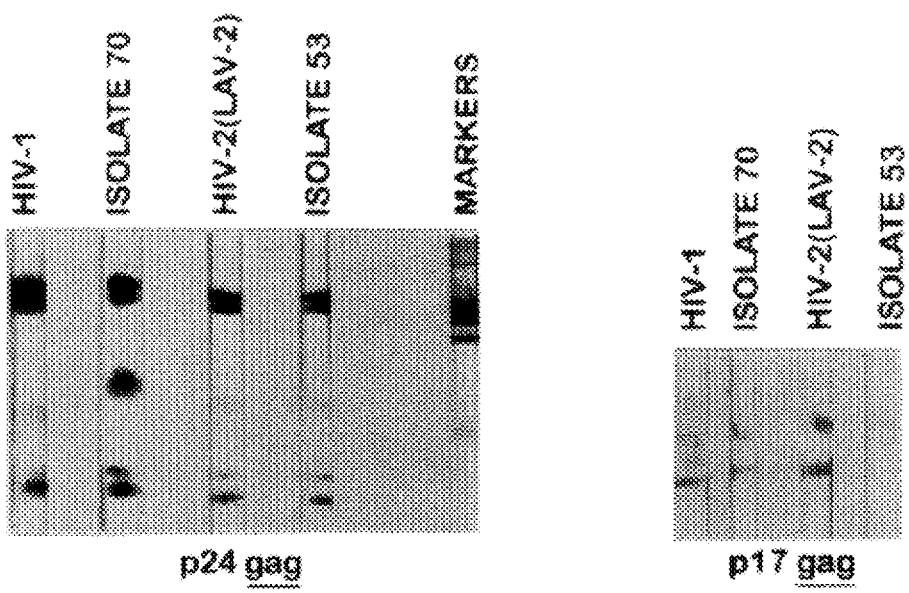
Figure 13D:
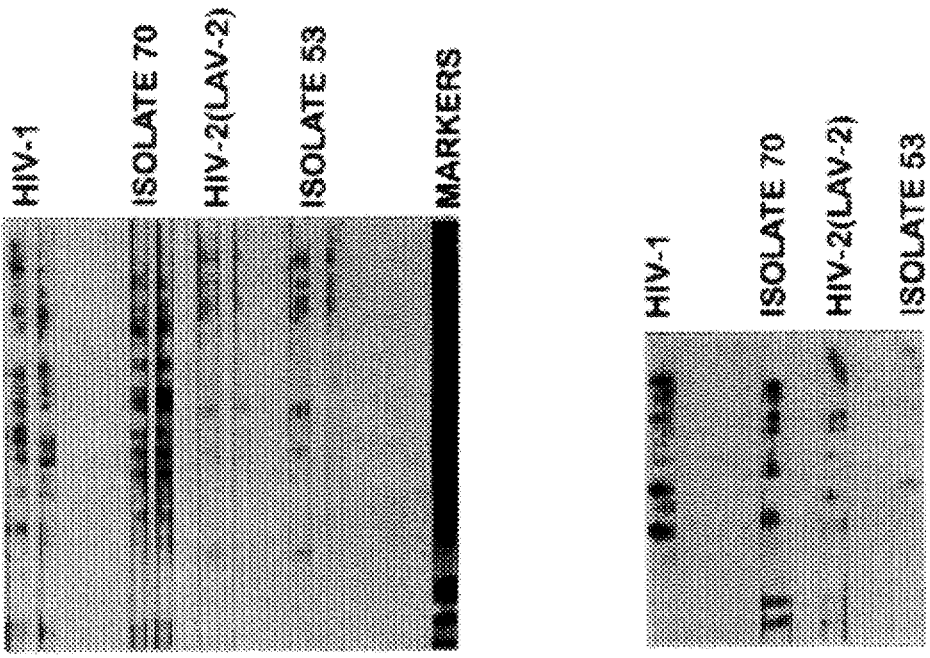

FIG. 13A and FIG. 13B are a comparison of partial cleavage products of gag and pol gene products of HIV-1 (SF4) [HIV-1 in the figure], HIV-3 (ANT 70) [isolate 70 in the figure], HIV-2rod [HIV-2 (LAV-2) in the figure] and HIV-2 (isolate 53) [isolate 53 in the figure]. The terms p24 and p17 are used in the genetic sense to indicate the largest and second largest viral core proteins, respectively.

FIG. 14A-I, FIG. 14A-II, FIG. 14A-III, FIG. 14B-1, FIG. 14B-II, and FIG. 14B-III shows hybridization of cDNA probes to viral RNA.

Viral RNA from HIV-1 (SF4), HIV-2rod, and HIV-3 (ANT 70) were spotted onto a membrane filter as described in Materials and Methods. The filters were hybridized under either nonstringent (A) or stringent conditions (B) and autoradiographed.

1. MORPHOLOGY

Electron microscopy of HIV-3-infected MT4 cells revealed the presence of extracellular virus particles having a diameter of approximately 120 nm and consisting of an outer envelope which surrounds an inner elongated core which has a diameter of approximately 20 to 40 nm and which appears in some thin sections to be slightly cone-shaped in contrast to the more or less cylindrical appearance of the HIV-1 core. Nevertheless, HIV-3 is morphologically very similar to HIV-1 and HIV-2 but is readily distinguished from other human retroviruses such as HTLV-1 and HTLV-II.

2. PROTEIN AND GLYCOPROTEIN ANTIGENS

The virus present in the culture supernatant of HIV-3-infected Molt-4 cells was concentrated by precipitation with polyethyleneglycol (average molecular weight 6000) followed by centrifugation. The resulting pellet was resuspended in phosphate buffered saline, layered on top of a 20% sucrose cushion and pelleted at 100,000 g for 1.5 hours. The pelleted virus was then dissociated in 62.5 mM Tris, pH 6.7, containing 2% 2-mercaptoethanol, 1% sodium dodecyl sulfate and 10% glycerol and the principle viral antigens were separated by electrophoresis on a polyacrylamide gel (12.5%) under denaturing-conditions. Molecular weight markers were included on the same gel so as to provide a basis for estimating molecular weights. Once separated, the proteins were electrophoretically transferred to nitrocellulose paper (Western blot) which was then incubated with an antiserum derived from a person infected with an HIV. In the initial experiments, a high titer antiserum was used from an individual who was infected with HIV-1 and which had been previously shown to crossreact with HIV-2 gag and pol-derived proteins. In this manner, the molecular weights of the HIV-3 gag and pol gene products could be compared with those of HIV-1 and HIV-2.

The apparent molecular weights observed for the HIV-3 proteins are close to those observed for both HIV-1 and HIV-2. Nevertheless, small yet reproducible molecular weight differences between HIV-3, and HIV-1 and HIv-2 proteins are also evident.

The protein blots revealed that HIV-3, like HIV-1 and HIV-2, possesses three core proteins. In the case of HIV-3, these proteins were found to have molecular weights of approximately 12,000, 16,500 and 25,000 respectively. By convention, proteins are frequently referred to by a "p" for protein or "gp" for glycoprotein, followed by a number which, when multiplied by 1,000, gives the approximate molecular weight of the polypeptide. The three major core proteins of HIV-3 will be referred to hereafter as p12, p16, and p25 respectively.

Figure 5:
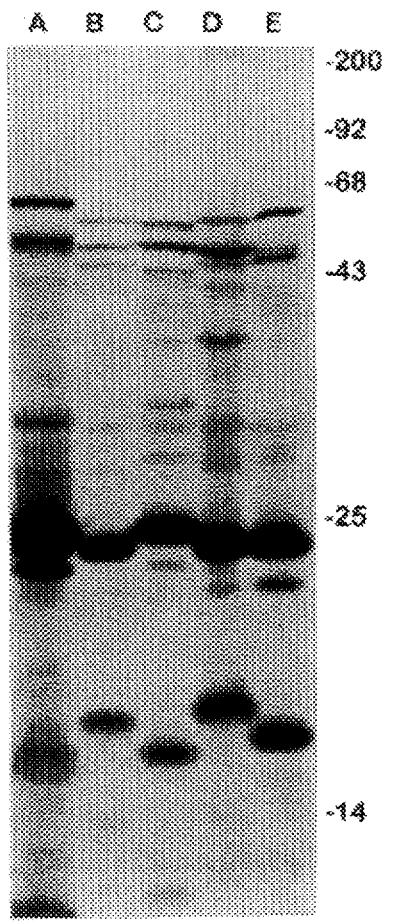

The molecular weight values as determined are expected to be correct to within 10% of the true values. Nevertheless, much confusion exists with regards to molecular weight values of proteins since the construction of the electrophoresis apparatus used and the source of the buffer components varies from laboratory to laboratory. It is therefore necessary when comparing the apparent molecular weights of the protein antigens of HIV-3 with respect to those of HIV-1 or HIV-2, to subject all samples to electrophoresis on the same gel. Such a gel can, for example, be seen in FIG. 5. In particular, it is evident that while, in the case of the major core protein, the molecular weight values of the homologous proteins of the three HIVs are very close, the protein derived from HIV-1 is the smallest. The major core protein of HIV-2 is somewhat larger then that of HIV-1, as has been previously reported. The homologous protein from HIV-3 is slightly larger than the major core protein of HIV-2. The calculated molecular weights of these proteins are given in Table 1.

TABLE 1

Comparison of molecular weights of gag and pol gene products.

|  | gag | | | ENDO | pol REVERSE TRANSCRIPTASE** | env TRANS MEMBRANE PROTEIN | OUTER MEMBRANE PROTEIN |
|---|---|---|---|---|---|---|---|
| HIV-1 | 12 KD | 17* KD, | 24 KD | 31 KD | 49 KD/65 KD | gp41 | gp120 |
| ANT 70 | 12 KD | 16.5 KD, | 24.8 KD | 31 KD | 48.5 KD/62 KD | gp41 | gp120 |
| HIV-2 | 12 KD | 16 KD, | 24.3 KD | 31 KD | 53 KD/69 KD | gp41 | gp120 |

TABLE 1-continued

Comparison of molecular weights of gag and pol gene products.

| | | pol | env | |
| | | REVERSE | TRANS MEMBRANE | OUTER MEMBRANE |
| gag | ENDO | TRANSCRIPTASE** | PROTEIN | PROTEIN |

*Some strain to strain variation in molecular weight has been observed for this protein.
**Molecular weights are given for both species of reverse transcriptase.

Similarly, molecular weight differences are also apparent between the three HIVs with respect to the second core protein which has, in most HIV-1 strains, a molecular weight of 18,000. Strain to strain differences in the molecular weight of this protein have, however, been documented in the case of HIV-1, and the molecular weight of this protein may be 17,000 in some isolates. The homologous protein from HIV-2 has a molecular weight of approximately 16,000 while the HIV-3 protein has an intermediate molecular weight of approximately 16,500.

By analogy with HIV-1 and HIV-2, HIV-3 also possesses two forms of the virally encoded enzyme reverse transcriptase. These two species also differ slightly in molecular weight from the corresponding species in HIV-1 and HIV-2 and are characteristic for HIV-3. These molecular weights are also summarized in Table 1.

HIV-3 possesses an additional pol gene-derived polypeptide which is an endonuclease with apparent molecular weight of 31,000 and which does not differ significantly in molecular weight from the homologous proteins from HIV-1 or HIV-2.

When protein blots containing HIV-3 proteins are incubated with serum obtained from an individual infected with this virus, two additional proteins can be seen. These proteins are derived from the env gene and are the viral envelope glycoproteins. The smallest protein, which is the transmembrane protein, migrates as a broad band with an apparent molecular weight of between 40,000 and 45,000. This protein will henceforth be referred to as gp41, with the understanding that the protein exhibits some intrinsic heterogeneity with respect to its apparent molecular weight and migration on polyacrylamide gels. The larger protein, which is the outer membrane protein, is similarly somewhat diffuse on polyacrylamide gels and has a molecular weight of approximately 120,000. This protein will henceforth be referred to as gp120. It should be noted that the apparent heterogeneous migration of these two species on polyacrylamide gel is not due to hetergeneity in the polypeptide chain but rather in posttranslational glycosylation. In particular, the gp120 is heavily glycosylated and the apparent molecular weight which one observes is to some degree influenced by the cell line used to produce the virus.

In addition to the Western blot, viral protein antigens can also be visualized by radioimmunoprecipitation assay (RIPA). For this purpose, viral proteins can be radioactively labeled metabolically in vivo by culturing HIV-3-infected cells in the presence of 35S-cysteine and 35S-methionine (200 Ci/ml) in RPMI 1640 medium devoid of these two amino acids and supplemented with dialyzed fetal calf serum. After 16 hours, the labeled virus is harvested from the culture supernatant by centrifugation over a 20% sucrose cushion at 100,000 g for 1.5 hours. The resulting pelleted virus is then resuspended in RIPA buffer (20 mM triethanolamine, pH 8.0, 0.5M NaCl, 0.5% Nonidet P40, 0.1% sodium deoxycholate, and 1 mM phenylmethylsulfonylfluoride).

Alternatively, the virus may be radioactivly labeled with 125 I using chloramine T by the technique familiar to persons versed in the art. In this case, virus is purified from the supernatant of infected cells by pelleting the virus through a cushion of 20% sucrose, resuspending the virus in phosphate buffered saline and banding the virus by ultracentrifugation on a 20 to 50% sucrose gradient at 60,000 g for 12 hours. The banded virus can be located in the fractionated gradient either by reverse transcriptase assay or by an antigen capturing assay. The fractions containing virus are pooled and Triton X-100 is added to a concentration of 0.5%. The Triton X-100-lysed virus may then be iodinated.

For immunoprecipitations, 100,000–200,000 cpm of labeled viral protein in RIPA buffer is reacted with 5 microliters of a test serum in a volume of 200 microliters for 16 hours at 4° C. The resulting immune complexes are then bound to Protein A-Sepharose (Pharmacia), washed extensively, and the bound proteins eluted with electrophoresis sample buffer containing 1% SDS. The antigens are subsequently analyzed by electrophoresis followed by autoradiography.

The protein antigens of HIV-3 can be characterized with respect to those of HIV-1 and HIV-2 using two different but related approaches. On one hand, the antigens may be characterized on the basis of their ability to crossreact with antisera from persons infected with HIV-1 and HIV-2. On the other hand, antisera from persons infected with HIV-3, which contain antibodies produced in response to HIV-3 antigens, can be used to test crossreactivity to HIV-1 and HIV-2 proteins. The antigenic relationships between HIV-3, and HIV-1 and HIV-2 are substantially illustrated in the examples given below.

The results of these experiments indicate that HIV-3 is only distantly related to HIV-2 since crossreactivity is only observed with respect to the viral core proteins and pol gene products. No crossreactivity of the env gene products was observed when anti-HIV-2 antiserum was incubated with HIV-3 proteins or when anti-HIV-3 antiserum was incubated with HIV-2 proteins.

In contrast, HIV-3 is more closely related to HIV-1 since anti-HIV-3 antiserum crossreacts not only with the gag and pol gene products of HIV-1 but also to some extent with the gp41 and gp120 env gene products, albeit with a lower affinity. Anti-HIV-1 antiserum similarly crossreacts with all of the protein antigens of HIV-3, but with a lower affinity than for the proteins of HIV-1.

In the examples which follow, it is demonstrated that HIV-3 is antigenically substantially different from HIV-1 on the basis of 1.) a different pattern of reactivity with anti-HIV-1 antiserum than that observed for HIV-1, 2.) a drastically reduced ability to be recognized by mouse monoclonal antibodies raised against the HIV-1 p24 and p17 core proteins, and 3.) preferential recognition of HIV-3 proteins, including the envelope proteins, over HIV-1 proteins by antisera from HIV-3-infected individuals.

In spite of the genetic variation characteristic of human immunodeficiency viruses, a test based, for example, on HIV-1 proteins derived from a particular strain will function satisfactorily for detecting antibodies raised in response to other HIV-1 variants. This can, in particular, also be seen in the example in which monoclonal antibodies were tested for their ability to react with antigens derived from HIV-1, HIV-2 and HIV-3 isolates. In this case, the monoclonal antibodies were raised against the core proteins from the HIV-1 IIIB strain, yet react very strongly to proteins derived from HIV-1 strain SF4. In contrast, these same monoclonal antibodies react only weakly or not at all with HIV-3 core proteins. This indicates that the antigenic differences between HIV-1 and HIV- 3 are of such a magnitude that immunological assays based on the use of HIV-5 proteins will not be suitable for testing sera from individuals infected with HIV-3.

Finally, in the examples given below, differences have been shown in the number and/or positions of methionine and tryptophan residues in the most highly conserved gag and pol gene products.

3. HIV-3 NUCLEIC ACIDS

A. HIV-3 viral RNA

The RNA of HIV-3 when deposited on a Hybond-H (Amersham) filter according to the "dot blot" technique, did not hybridize to HIV-1 DNA under stringent hybridization conditions.

By "stringent conditions" or "nonstringent conditions" are meant the conditions under which the actual hybridization and/or the subsequent wash steps are performed. Dot blot hybridizations were performed by spotting dilutions of viral RNA from HIV-1 strain SF4, HIV-2 rod and HIV-3 strain ANT 70 onto Hybond-H filters.

The dilution series for each virus corresponded to viral RNA pelleted from the equivalent of 5, 2.5, 1.25 and 0.62 milliliters of culture supernatant. The RNA was fixed onto the filter by U.V. irradiation for 2 min and subjected to hybridization by bringing the filter into contact with a 32P-labeled DNA probe. The probe chosen was derived from the HIV-1 sequence spanning nucleotides 487–4652 (Sac I-Eco R1) and includes a portion of the 5' long terminal repeat, the entire gag region and most of the pol gene, subcloned in the vector pUC 13. Hybridization of the 32P-labeled probe with the filter was carried out under stringent conditions in 3×SSC, 0.5% milk powder, 1% SDS, 10% dextran sulfate, 50% formamide (volume/volume) at 42° C. for 18 hrs (1×SSC corresponds to 0.15M NaCl, 0.015M sodium citrate). The subsequent wash steps were carried out under stringent conditions in 0.1×SSC and 0.1% SDS at 65° C. (2–30 minute washes). The filter was then dried and autoradiographed with enhancing screens at −70° C. Following autoradiography, only spots were visible which corresponded to HIV-1 viral RNA. No hybridization was observed to HIV-2 or either of the two HIV-3 strains. HIV-3 therefore appears to be only distantly related to HIV-1.

B. cDNA and subclones of cDNA derived from HIV-3

The conditions under which cDNA corresponding to HIV-3 sequences was synthesized and cloned are described below. HIV-3 (strain ANT 70) from 1 liter of culture was precipitated with polyethylene glycol 6000, redissolved in phosphate buffered saline, and pelleted through a 20% sucrose cushion. The resulting virus pellet was dissolved in 6M guanidinium chloride in 20 mM dithiothreitol and 0.5% Nonidet P-40. CsCl was added to a concentration of 2 molar and the solution containing disrupted virus was layered onto a 1.2 milliliter cushion of 5.7M CsCl containing 0.1 EDTA. Viral RNA was pelleted by centrifuging for 20 hrs. at 25,000 rpm in a Beckman SW28 rotor at 15° C. The pelleted RNA was redissolved, extracted with phenol and precipitated with ethanol and 2M LiCl.

One-fifth of the viral RNA, prepared as described above, was used to direct the first step in the synthesis of cDNA which made use of an oligo (dT) primer which served to prime the synthesis of the first cDNA strand.

A commercially available kit supplied by Amersham was used for preparation of HIV-3 cDNA and made use of an exogenously added reverse transcriptase to synthesize the first strand. The synthesis of the second strand was performed using *E. coli* DNA polymerase I in the presence of RNase H to digest away the RNA strand of the RNA/DNA hybrid.

Second strand synthesis was performed in the presence of 32p-dCTP to label the cDNA. The resulting cDNA was treated with T4 DNA polymerase to create blunt ends, the cDNA was methylated to protect possible internal EcoRI cleavage sites, and was then coupled to EcoRI linkers, also supplied by Amersham. The EcoRI restriction sites were then cleaved and the cDNA was sized on a 1.2 a agarose gel. The region in the gel corresponding to a cDNA length of 500 to 2000 base pairs was excised and the cDNA was eluted and cloned in the vector pUC13 which had been cleaved with EcoRI and dephosphorylated. The DNA was then used to transform competent cells of *E. coli* MC1016 (lambda). The resulting colonies were transferred to Pall membranes (Pall Biodyne), lysed and denatured with 1.5M NaCl, 0.5M NaOH and neutralized with 3M NaOAc, pH 5.5. Screening of colonies harboring an insert of HIV-3 was performed under moderately stringent conditions in a buffer containing 5×SSC, 5×Denhardts solution, 0.2% SDS, 250 mg/ml denatured salmon sperm DNA, overnight at 65° C., using 32P-labeled plasmid containing the SacI-EcORI fragment of HIV-1 discussed above. Following hybridization, filters were washed as follows:

1. 1 hour in 2×SSC, 0.1% SDS at room temperature.
2. 30 minutes in 0.1×SSC, 0.1% SDS at room temperature.
3. 20 minutes in 2×SSC, 0.1 SDS at 42° C.
4. 20 minutes in 0.1×SSC, 0.1% SDS at 420° C.

Following autoradiography of the filter, several weakly positive colonies were identified which were then grown for analysis. It was expected that the positive signal would either be due to weak homology with the gag or pol regions of HIV-1, or due to some sequence homology with the R region of the LTR.

C. Sequences contained in HIV-3 cDNA.

A clone carrying the largest insert, which was found to be 906 base pairs in length and is referred to as iso 70-11, was selected for sequence analysis. A number of subclones of the insert were prepared by digesting the insert with various restriction enzymes and subcloning the resulting fragments in the pUC 13 vector. Sequence determinations were performed according to the dideoxy-method, described by Sanger, (Proc. Natl. Acad. Sci. U.S.A. 74: 5463–5467, 1977), using a kit purchased from Boehringer which makes use of 17-mer M13 primers. Sequence analysis of cDNA clone iso 70-11 revealed that the insert corresponded to the 3' end of the viral genome which possessed a poly (A) chain at the 3' end.

The HIV-3 retrovirus contains a 3' LTR which is composed of a U3 region as well as an R region. Like the 3' LTR region of HIV-1, clone iso 70-11 contains an AATAAA polyadenylation signal located approximately 23 nucleotides from the 3' end of the R region. Analysis of the HIV-3 sequence revealed approximately 70% homology with the corresponding 3' LTR sequence of HIV-1 and less than 55% homology with the corresponding sequence of HIV-2.

Conversely, hybridizations using HIV-1 gag-pol sequences as the labeled probe to detect crosshybridization with HIV-3 RNA revealed no detectable hybridization when the hybridization was carried out under stringent conditions. This again indicates that the viruses are only distantly related and that a distinction can be made between HIV-1 and HIV-3 at the nucleic acid level in the region of the genome encompassing the gag and pol genes. This same labeled probe did, however, hybridize to RNA derived from HIV-1 strain SF4.

In addition, the invention relates to a composition comprising at least one antigen, in particular, a protein or glycoprotein of HIV-3 retrovirus. Such a composition can be used in methods for detecting antibodies and in kits for carrying out such methods.

The HIV-3 virus has proven to be a usable as a source of antigen for detecting antibodies in people who have come into contact with HIV-3. As such, the virus may be grown and concentrated by the methods already described and a lysate prepared by treating the virus with a suitable detergent. A preferred detergent for preparing a total viral lysate is Triton X-100, used at a concentration of 0.5%. Another preferred detergent is Nonidet P-40 (NP-40), also used at a concentration of 0.5%.

Alternatively, viral protein may be purified from lysates of the virus. A preferred method for purifying these proteins is affinity chromatography. For example, the viral antigens may be separated on a preparative polyacrylamide gel and the individual antigens eluted in purified form. These may further be used to raise antisera in, for example, rabbits which are specific for the individual viral proteins. The IgG fraction derived from immune rabbit serum can be coupled to a solid phase such as CNBr-activated Sepharose 4B (Pharmacia) and used to selectively remove individual viral antigens from viral lysates. These proteins may then be eluted from the affinity support using a low pH buffer and further purified using standard chromatographic techniques of which an example is given by Montelaro et al., J. of Virology (1982) 42: 1029-1030.

The invention relates generally to any composition which can be used for the diagnosis of HIV-3 infection or for tests which have a prognostic value. These diagnostic procedures involve the detection of antibody in serum or other body fluid, which are directed against at least one of the antigens of HIV-3.

Preferred compositions are viral lysates or purified antigens which contain at least one of the viral core proteins, p12, p16, and p25 or envelope proteins gp41 or gp120, or pol gene-derived proteins, such as p31. Especially preferred compositions are those which simultaneously contain, by way of example, the following proteins, p25 and gp120
p25 and gp41
p25, gp41 and gp120
p12, p16 and p25
p25, p31 and gp120

It should be understood however, that the above mentioned compositions are only meant to serve as examples and that the invention relates to all lysates or protein preparations containing one or more of the above mentioned proteins or glycoproteins.

The invention also relates to any composition in which either HIV-3 viral lysate is used in combination with similarly prepared proteins derived from HIV-1 and/or HIV-2 for the general diagnosis of infection or contact with human immunodeficiency virus without regard to the absolute identity of the virus being detected. For example, such compositions could consist of a mixture of lysates of HIV-1, HIV-2 and HIV-3 or could consist of the following:

core proteins of HIV-1, HIV-2 and HIV-3, and in particular the major core protein of each virus type, homologous to the HIV-3 p25 protein.

envelope glycoproteins of HIV-1, HIV-2 and HIV-3 and in particular the outer envelope glycoproteins of each virus type, homologous to HIV-3 gp120.

core proteins of HIV-1, HIV-2 and HIV-3 together with the envelope glycoproteins of HIV-1, HIV-2 and HIV-3, in particular the major core protein of each virus type, homologous to the HIV-3 p25 protein, together with the major outer envelope protein of each virus, homologous to HIV-3 gp120.

a combination of the core proteins and envelope proteins of HIV-1, HIV-2 and HIV-3 and in particular homologous to the HIV-3 proteins p25 and gp120 respectively and a protein derived from the pol gene of HIV-1, HIV-2 and HIV-3, in particular the proteins of each virus type homologous to the p31 endonuclease protein of HIV-3.

Furthermore, the invention relates to an antigen providing a single band in polyacrylamide gel electrophoresis, said antigen comprising, in common with one of the purified antigens of HIV-3 retrovirus, an epitope that is recognized by serum of persons carrying anti-HIV-3 antibodies. The amino acid sequences corresponding to these epitopes can readily be determined by isolating the individual proteins either by preparative electrophoresis or by affinity chromatography and determining the amino acid sequence of either the entire protein or the fragments produced enzymatically by trypsin or chymotrypsin digestion or chemically by the procedures described in detail below. The resulting peptide or polypeptides can subsequently be sequenced by Edman degradation. The invention relates therefore to any protein, glycoprotein op peptide, either derived directly from the virus or produced by cloning any cDNA fragments of the virus in bacterial expression vectors, or viral expression vectors for the expression of inserted DNA in mammalian or insect cells, and purifying the expressed protein by the methods described above. Furthermore, the invention also relates to synthetic peptides, produced either by Merrifield synthesis or Fmoc chemistry, which may be subsequently purified to homogeneity and which contain in their sequences epitopes which are shared by the natural HIV-3 antigens.

Antigens which share epitopes with viral proteins may easily be recognized by their reaction with antibodies present in the serum of individuals infected with HIV-3, either by Western blotting, or radioimmunoprecipitation. In the case of small peptides which are not able to bind to nitrocellulose, these peptides can be detected by binding to nylon membranes (Pall Biodyne or Amersham) and reacting the membrane with anti-HIV-3 antiserum. In particular, the invention relates to epitopes contained in any of the HIV-3 core proteins, p12, p16 and p25 or in a protein which may contain as part of its polypeptide chain epitopes derived from a combination of the core proteins. Furthermore, the invention relates to epitopes contained in either of the two HIV-3 envelope glycoproteins, gp41 and gp120 as well as any protein which contains, as part of its polypeptide chain, epitopes derived from a combination of the HIV-3 envelope glycoprotein or a combination of the HIV-3 envelope glycoproteins and HIV-3 core protein. The invention additionally relates to polypeptides whose synthesis is directed by expression vectors constructed by recombinant DNA methods which incorporate epitopes derived from HIV-3 proteins or glycoproteins together with epitopes derived from the proteins or glycoproteins of either HIV-1 and/or HIV-2 into a single polypeptide chain. Preparing such a construction would involve excising the relevant coding regions from cDNA of HIV-3 as well as HIV-1 and HIV-2, and coupling the DNA in phase so as to form a coding sequence which, when inserted into an expression vector possessing the necessary signal sequences, directs the synthesis of a hybrid protein in which epitopes of the HIV-3, HIV-1 and HIV-2 are contained.

Furthermore, the invention relates to methods for the detection of antibodies against HIV-3 retrovirus in a biological fluid, in particular for the diagnosis of a potential or existing ARC or AIDS caused by HIV-3 retrovirus, characterized by contacting body fluid of a person to be diagnosed with a composition containing one or more of the proteins or glycoproteins of HIV-3 or with a lysate of the virus, or with an antigen possessing epitopes common to HIV-3, and detecting the immunological conjugate formed between the anti-HIV-3 antibodies and the antigen(s) used.

Preferred methods include, for example, immunofluorescence assays or immunoenzymatic assays.

Immunofluorescence assays typically involve incubating, for example, serum from the person to be tested with cells infected with HIV-3 and which have been fixed and permeabilized with cold acetone. Immune complexes formed are detected using either direct or indirect methods and involve the use of antibodies which specifically react to human immunoglobulins. Detection is achieved by using antibodies to which have been coupled fluorescent labels, such as fluorsecein or rhodamine.

Immunoenzymatic assays may be performed, for example, as follows:

- a specific quantity of HIV-3 virus extract or of a composition referred to according to the invention is deposited in the wells of a microtitration plate.
- the excess unbound material is removed after a suitable incubation period by washing.
- a suitable dilution or dilutions of serum of other body fluid which is to be tested for the presence of antibodies directed against one or more of the protein or glycoprotein antigen of HIV-3 is introduced into the well.
- the microtitration plate is incubated for a period of time necessary for the binding reaction to occur.
- the plate is washed thoroughly.
- the presence of immune complexes is detected using antibodies which specifically bind to human immunoglobulins, and which have been labeled with an enzyme, preferably but not limited to either horseradish peroxidase, alkaline phosphatase, or beta-galactosidase, which is capable of converting a colorless or nearly colorless substrate into a highly colored product. Alternatively, the detection system may employ an enzyme which, in the presence of the proper substrates, emits light.
- the amount of product formed is detected either visually, spectrophotometrically, or luminometrically, and is compared to a similarly treated control.

Other detection systems which may also be used include those based on the use of protein A derived from Staphylococcus aureus Cowan strain I, protein G from group C Streptococcus sp. (strain 26RP66), or systems which employ the use of the biotin-avidin binding reaction.

Another method of immunoenzymatic detection of the presence of antibodies directed against one or more of the HIV-3 antigens is the Western blot. The viral antigens are separated electrophoretically and transferred to a nitrocellulose membrane or other suitable support. The body fluid to be tested is then brought into contact with the membrane and the presence of the immune complexes formed is detected by the method already described. In a variation on this methods, purified viral antigen is applied in lines or spots on a membrane and allowed to bind. The membrane is subsequently brought into contact with the body fluid to be tested and the immune complexes formed are detected using the previously described techniques.

The presence of antibodies in body fluid may also be detected by agglutination. HIV-3 lysates or a HIV-3 lysate, antigen or purified antigen composition referred to according to this invention, is used to coat, for example, latex particles which form an uniform suspension. When mixed with serum containing antibodies to the antigen present, the latex particles are caused to agglutinate and the presence of large aggregates can be detected visually.

The present invention also relates to labeled extracts of HIV-3 or compositions as previously described. The labeling can be of any type, such as enzymatic, chemical, fluorescent or radioactive.

Furthermore, the invention relates to a method for detecting the presence of HIV-3 antigens in body fluids. This may, for example, be accomplished in the following manner:

- the IgG fraction of antiserum, derived either from humans infected with HIV-3 or from animals injected with an HIV-3 lysate or composition already described, is placed in the wells of a microtitration plate.
- after a suitable period to allow adsorption, the excess unbound material is washed away.
- a body fluid containing the antigen to be detected is placed in the well.
- the microtitration plate is allowed to incubate for a suitable period of time to allow binding to occur.
- the plate is then thoroughly washed with a suitable buffer.
- the presence of bound antigen is detected either directly or indirectly, for example, by using immunoglobulins which are similarly specific for the antigen(s) to be detected and which have been labeled, preferably with one of the aforementioned enzymes.
- an appropriate substrate is then added and the extent of reaction is compared to a control in order to measure the amount of antigen present.

Furthermore, the invention relates to a kit for the detection of anti-HIV-3 antibodies in biological fluids, comprising an HIV-3 lysate or a composition as referred to above and a means for detecting the immunological complexes formed.

In the case of kits designed to detect specific antibodies by immunoenzymatic methods such a kit would include:

- an HIV-3 lysate or composition of one of the types already described, preferably in a purified form, and preferably attached to a solid support such as a microtitration plate.
- a conjugate between an enzyme and an immunoglobulin fraction which is capable of binding to the antibodies to be detected, or a conjugate between an enzyme and bacterial protein A or protein G.
- a control antigen which possesses no epitopes which are shared by any human immunodeficiency virus.

appropriate buffers for performing the assay.

an appropriate substrate for the enzyme.

Kits for the detection of specific antibodies which make use of labeled antigen would include:

- an appropriately labeled antigen or combination of antigens of the types already described.
- protein A or anti-human immunoglobulins, preferably coupled to an insoluble support, such as Protein A-Sepharose 4B (Pharmacia) or an equivalent support.
- control antigen, which is not recognized by anti-HIV-3 antisera.
- appropriate buffers for performing the assay.
- if appropriate, substrates for the detection of enzymatically labeled antigen.

The invention further relates to kits, developed for the detection of HIV-3 antigens in biological fluids, which comprise

- anti-HIV-3 immunoglobulins, preferably coupled to a solid support such as a microtitration plate.
- anti-HIV-3 immunoglobulins conjugated to an enzyme.
- negative control antigen, which would not be recognized by anti-HIV-3 immunoglobulins.
- positive control antigen which consists of one of the HIV-3 antigens or compositions already described.
- appropriate buffers for conducting the test.
- an appropriate substrate for detection of bound enzyme.

Furthermore, the invention relates to an immunogenic composition containing an envelope glycoprotein of HIV-3 retrovirus, in particular, gp41 or gp 120, or a part of said glycoprotein, in combination with a pharmaceutically acceptable vehicle suitable for the constitution of vaccines effective against HIV-3. The invention additionally relates to any peptide or polypeptide which contains within its sequence all or part of the protein backbone of the HIV-3 retrovirus, as well as peptides which result from addition, substitution, or deletion of amino acids which do not affect the general immunological properties of said peptides.

The invention further relates to monoclonal antibodies characterized by their ability to specifically recognize epitopes contained in the HIV-3 antigens or compositions as previously defined, and in particular, monoclonal antibodies raised specifically against said antigens and produced by traditional techniques. The invention also relates to monoclonal antibodies of human origin produced by immortalizing B-cells derived from persons infected with HIV-3, for example, by transforming the B-cells with Epstein-Barr virus and subcloning the transformants.

The invention likewise relates to the production of polyclonal antisera in animals which recognize one or more HIV-3 antigens and which is produced by infecting animals with purified HIV-3 or an HIV-3 antigen or combination of antigens, and in particular the proteins or glycoproteins of HIV-3.

The antibodies, either polyclonal or monoclonal, can be used for a wide variety of purposes which include neutralization of HIV-3 infectivity, the detection of HIV-3 antigens in biological fluids or in infected cells, and the purification of HIV-3 protein and glycoprotein antigens.

The invention further relates to nucleic acids, optionally labeled which are derived in part, at least, from RNA of HIV-3 retrovirus or of variants of this virus.

The invention relates likewise to the use of cDNA or parts of the cDNA or the recombinants containing them, which are characterized by containing at least a portion of the cDNA corresponding to the entire genomic RNA of the HIV-3 retrovirus. Such cDNAs may be used as probes for the specific detection of HIV-3 sequences in biological fluids, tissues and cells. The probes are preferably also labeled, either radioactively or chemically, alternatively using enzymatic, fluorescent or chemiluminescent labels which enable the probes to be detected. Preferred probes for the specific detection of HIV-3 and diagnosis of HIV-3 infection are probes that contain all or a portion of the CDNA complementary to the HIV-3 genome. In this context, an especially advantageous probe can be characterized as one which contains, in particular, the nucleic acid sequence contained in clone iso 70-11 and which includes the viral LTR-R sequence which is located at both the 5' and 3' ends of viral genomic RNA and at both the 5' and 3' ends of integrated proviral DNA.

It is nevertheless understood that the probes which can be used for the diagnosis of HIV-3 infection are in no way limited to the probes described above, and that the invention incorporates all sequences which originate from the HIV-3 genome or its naturally occurring variants and includes sequences encoding the viral core proteins (gag gene),the two forms of reverse trancriptase and the endonuclease (pol gene), as well as the two viral envelope glycoproteins (env gene).

The invention also relates to HIV-3 nucleic acid sequences which have been incorporated into a recombinant nucleic acid comprising a nucleic acid from a vector, and having said cDNA or part of said cDNA inserted therein. Such a construction could be used for replicating the viral cDNA or its fragments in an organism or cell other than the natural host so as to provide sufficient quantities of the probe to be used for diagnostic purposes.

A probe generated in such a manner can be employed in a diagnostic test for specific detection of HIV-3 which incorporates the following essential steps

- labeling of the probe generated as described above by the methods previously described.
- bringing the probe into contact under stringent hybridization conditions with DNA from infected cells or viral RNA from infected cells or biological fluids, once said DNA or RNA has been, preferably, applied to a membrane and has been rendered accessible to the probe.
- washing the membrane with a buffer under circumstances in which stringent conditions are maintained.
- detection of the labeled probe, preferably by autoradiography in cases in which the probe has been radioactively labeled, or by a suitable immunodetection technique in case the probe has been labeled chemically.

The invention further relates to a process for the production of HIV-3 retrovirus characterized by culturing human T4 lymphocytes or human lymphocytic cell lines of leukemic origin which carry the T4+phenotype with lymphocytes or cell lines that have previously been infected with an isolate of HIV-3 retrovirus, as well as recovering and purifying the retrovirus from the culture medium. The invention likewise relates to a process for the production of antigens of HIV-3 retrovirus, characterized by lysing the retrovirus, preferably with a detergent, and recovering the lysate containing said antigens.

The invention additionally relates to a process for the production of any of the HIV-3 proteins or glycoproteins p12, p16, p25, p31, gp41, gp120 or reverse trancriptase as previously defined, or a part thereof, characterized by inserting the nucleic acid encoding the proteins or glycoproteins in an expression vector, transforming a host with said vector, culturing the transformed host as well as recovering and purifying the expressed protein. The process includes vectors which may or may not direct the synthesis of fusion proteins and includes but is not limited to bacterial expression vectors, mammalian expression vectors such as vaccinia virus, and vectors based on baculovirus for the expression of cloned genes in insect cells.

EXAMPLES

MATERIALS AND METHODS

Virus and cell culture a. Virus strains and cell lines

HUT-78 cells chronically infected with ARV-4 (HIV-1 SF4), originally isolated by J. Levy, San Francisco, U.S.A. (20) and uninfected HUT-78 cells were kindly provided by S. Sprecher, Brussels, Belgium. LAV-2rod originally from L. Montagnier, Paris, and CEM cells were obtained from J. De Smeyter, Leuven, Belgium. Isolate 53, an HIV-2 isolate, was isolated in this laboratory (21).

b. Virus isolations

Virus isolations were performed in a manner similar to that described by Levy and Shimabukuro (22), with modifications. Lymphocytes from patients as well as from healthy donors were isolated from heparinized whole blood on Lymphoprep (Nyegaard and Co., Oslo, Norway) and were cultured in RPMI 1640 containing 20 mM HEPES, 15 percent fetal calf serum (Gibco), 5 g/ml hydrocortisone (Merck), 75 U/ml IL-2 and 2 g/ml polybrene (Aldrich).

Lymphocytes from healthy donors were stimulated with 2 g/ml phytohemagglutinin (PHA, Wellcome) for 3 days prior to use. Fresh PHA-stimulated lymphocytes were added to the virus isolation cultures every 3 to 4 days. Cultures were monitored for cytopathic effect, immunofluorescence, using a broad specificity, polyclonal reference antiserum (23), and the presence of antigen in the culture supernatants (Innotest VCA-HIV, Innogenetics). The broad specificity reference (BSR) anti-serum used was derived from an HIV-1-infected donor and was shown experimentally to have an exceptionally high titer ($\geq 1,000,000$ in an enzyme immunoassay based on recombinant HIV-1 p24 protein) and to crossreact strongly with the gag and pol gene products of other HIV types, in particular, HIV-2. Reverse transcriptase was also assayed essentially as described (24).

In order to establish chronically infected, permanent cell lines, virus-infected primary lymphocytes were co-cultured with Molt 4 clone 8 cells (25), kindly provided by N. Yamamoto, Yamaguchi, Japan, and monitored for cell growth. Virus production was monitored by the reverse trancriptase assay as well as antigen capturing.

Differential antigen capturing

A test system was developed whereby a distinction can be made between HIV-1 and other related human immunodeficiency viruses. The system is based on a comparison of the ability of two different polyclonal IgG preparations, one with a broad anti-HIV specificity which is due its exceptionally high titer, particularly against the major core protein, and one with a lower titer which reacts preferentially with HIV-1, to capture detergent-treated virus in culture supernatants. Detection of captured antigen is achieved by using a (broad specificity IgG)/horseradish peroxidase conjugate.

The test detects primarily but not exclusively the p24 core protein.

Monoclonal antibodies to HIV-1

The panel of monoclonal antibodies used has been described (26). The antibodies were prepared against native viral proteins in Triton X-100-disrupted HIV-1 preparations.

Protein analysis a. Electrophoresis

Polyacrylamide gel electrophoresis of viral proteins was performed essentially as described by Maizel (27).

b. Protein blotting

Blotting was performed either in a Bio-Rad transblot cell at 400 mA for 4 hours using the carbonate buffer described by Dunn (28) or using the LKB semi-dry blotting apparatus at 0.8 mA/cm2 for 1 hour in 48 mM Tris, 39 mM glycine, 0.0375% sodium dodecylsulfate (SDS) and 20% methanol.

c. Generation of partial cleavage products

Viral proteins were analyzed by the technique shown in FIG. 1. Advantage was taken of the fact that corresponding proteins from the various isolates have similar molecular weights. Proteins were separated on 12.5 percent SDS-polyacrylamide gels together with a marker lane of ARV-4 proteins which was excised following electrophoresis, blotted and incubated with an anti-HIV antiserum to reveal the positions of the viral proteins.

The marker blot was in turn used to locate the approximate positions in the Coomassie blue stained portion of the gel of the viral proteins to be cleaved. Horizontal gel slices containing the proteins were excised, transferred to glass tubes and subjected to chemical cleavage.

1. Cyanogen bromide cleavage

The gel slice was incubated with 10 ml of a freshly prepared 40 mg/ml solution of CNBr (Merck) in 0.3N HCl for 3 hours at room temperature in a fume hood. Following the incubation, the gel slice was equilibrated with SDS-sample buffer for electrophoresis in the second dimension.

2. BNPS-Skatole cleavage

The gel slice was incubated with 10 ml of a freshly prepared saturated solution of 2-(-2'-nitrophenylsulfenyl)-3-methyl-3'-bromoindolinine (BNPS-Skatole, Pierce) in 70 percent acetic acid; 30% $H_2O$ containing 0.1% phenol, for 3 hours at room temperature, protected from light. Following the incubation, the gel slice was equilibrated by repeated washing in SDS-electrophoresis sample buffer.

Following cleavage, the individual lanes were excised from the gel slices, rotated 900 and placed on top of a 10 to 20 percent SDS-polyacrylamide gradient gel. On completion of electrophoresis, the gel was blotted onto nitrocellulose (Schleicher and Schuell) and blocked with PBS containing 1 mg/ml casein (Merck). Only cleavage products with molecular weights in excess of 10 kD are able to be visualized since peptides with lower molecular weights do not bind efficiently to nitrocellulose. Blots were incubated with a broad spectrum anti-HIV antiserum followed by goat anti-human IgG: alkaline phosphatase conjugate (Promega).

Partial cleavage products were then visualized by reaction with 5-bromo-4-chloro-3-indolylphosphate and nitro blue tetrazolium (Sigma).

Viral Nucleic Acids a. Hybridization to viral RNA

Virus from culture supernatants was harvested by pelleting through cushions of 20% sucrose by centrifucation at 26,500 rpm for 1.5 hrs. at 4° C. and was disrupted in 10 mM Tris, pH 7.4, 10 mM NaCl, 10 mM EDTA containing 0.5% sodium dodecylsulfate. Aliquots of the disrupted virus were spotted onto a membrane of Hybond H (Amersham) in amounts corresponding to 5, 2.5, 1.25 and 0.62 milliliters of original culture supernatants. The RNA deposited onto the filter was fixed to the membrane by irradiation with ultraviolet light for 2 hrs. The RNA bound to the filter was then subjected to hybridization with an HIV-1 cDNA probe which had been labeled by nick translation with 32p-dCTP. The hybridization was carried out under stringent conditions in 3×SSC, 0.5% milk powder, 1% SDS, 10% dextran sulfate and 50% formamide at 42° C. for 18 hrs. Following hybridization, the filter was washed twice under stringent conditions in 0.1×SSC and 0.1% SDS for 30 minutes. Hybridization was detected by autoradiography at −70° C. with enhancing screens. Hybridizations were similarly performed using a probe derived from the env region of HIV-2.

Hybridizations were also performed under nonstringent conditions in 5×SSC, 25% formamide, 5×Denhardts solution, 10% dextran sulfate, and 100 g/ml denatured salmon sperm DNA at 37° C. overnight. The filter was subsequently washed 4 times for 15 minutes in 5×SSC, 0.1% SDS at room temperature and autoradiographed.

b. Preparation of ANT 70 cDNA

Virus was pelleted from 1 liter of culture supernatant using polyethylene glycol 6000, redissolved in PBS and pelleted through a 20% sucrose cushion. The resulting pellet of virus was disrupted in 6M guanidinium chloride in 20 mM sodium phosphate buffer, pH 6.5, containing 20 mM dithiothreitol and 0.5% NP-40. Solid CsCl was added to a concentration of 2 molar. The solution containing disrupted virus was layered onto a cushion of 5.7M CsCl containing 0.1M EDTA and the viral RNA was pelleted by centrifugation at 25,000 in a Beckman SW 28 rotor at 15° C. for 20 hrs. Following centrifugation, the RNA was redissolved, extracted with phenol and precipitated with ethanol and 2M LiCl.

One-fifth of the viral RNA prepared was used to direct the first step in the synthesis of cDNA using a kit supplied by Amersham. cDNA synthesis was primed using oligo (dT), the synthesis was carried out using the reverse trancriptase supplied with the kit. Second strand synthesis was performed using $E.$ $coli$ DNA polymerase I in the presence of RNase H to digest away the RNA strand of the RNA/DNA hybrid. The synthesis of the second strand was performed in the presence of 32P-dCTP to label the cDNA. The resulting cDNA was treated with T4 DNA polylmerase to create blunt ends, the cDNA was methylated to protect possible internal EcoRI cleavage sites, and was then coupled to EcoRI linkers (Amersham). The EcoRI sites in the linkers were then cleaved and the CDNA was sized on a 1.2% agarose gel. The region of the gel corresponding to a cDNA length of 500 to 2000 base pairs was excised, and the cDNA was eluted and cloned in the vector pUC13 which had previously been cleaved with EcoRI and dephosphorylated. After ligation, the DNA was used to transform competent cells of $E.$ $coli$ MC1016 (lambda). The resulting colonies were transferred to Pall membrane filters (Pall Biodyne), lysed and denatured with 1.5M NaCl, 0.5M NAOH and neutralized with 3M NaOAc, pH 5.5. Screening of colonies harboring an insert of HIV-3 was carried out by hybridization under moderately stringent conditions in 5×SSC, 5×Denhardts solution, 0.2% SDS, 250 mg/ml denatured salmon sperm DNA overnight at 65° C. Hybridization was performed using the HIV-1 SacI-EcoRI fragment. Following hybridization, the filters were washed as follows:

1. 1 h. in 2×SSC, 0.1% SDS at room temperature.
2. 30 minutes in 0.1×SSC, 0.1% SDS at room temperature.
3. 20 minutes in 2×SSC, 0.1% SDS at 42° C.
4. 20 minutes in 0.1×SSC, 0.1% SDS at 42° C.

After washing, the filters were autoradiographed at −70° C. using intensifying screens.

Hybridizations were also performed under the nonstringent conditions used for nonstringent hybridization of the HIV-1 and HIV-2 probe.

c. Analysis of cDNA clones

Colonies giving a positive hybridization signal were grown for analysis. Plasmids were isolated, cleaved with EcoRI and subjected to agarose gel electrophoresis to confirm the presence of an insert and to determine its size. Of 96 colonies analyzed 17 were found to contain inserts. Five were taken for further analysis and ranged in size from approximately 800 to 1600 base pairs in length.

d. Sequence determinations

Nucleotide sequence determinations were performed according to the dideoxynucleotide method of Sanger (Proc. Natl. Acad. Sci. U.S.A. 74: 5463–6467, 1977), using a kit supplied by Boehringer. Sequencing was carried out using 17-mer M13 primers.

e. Hybridizations of ANT 70 CDNA to HIV-1 and HIV-2 viral RNA.

The ANT 70 cDNA clone containing the largest insert (iso 70-11) was used for hybridization to the filter onto which viral RNAs had been deposited.

Hybridization was performed under stringent conditions in 3×SSC, 0.5% milk powder, 1% SDS, 10% dextran sulfate, and 50% formamide at 42° C. for 18 hrs. Following hybridization, the filter was washed with 0.1×SSC, 0.1% SDS at 65° C. (2–30 minute washes) after which the filter was autoradiographed at −70° C. with an intensifying screen.

Results

Virus isolation

As part of a continuing study on heterosexual transmission of HIV, a virus isolation was performed from blood from a Camerounian woman and her partner. As before, the two isolated strains will be named HIV-3 (ANT 70) (woman) and HIV-3 (ANT 70 NA) (man), respectively. For convenience, the shorter terms ANT 70 and ANT 70 NA will also be used. The woman is the partner of an HIV-seropositive man with generalized lymphadenopathy. Serum from the woman was moderately positive (ratio O.D./cut-off of 4.5) in the enzyme-linked immunosorbent assay (EIA, Organon Teknika) and had a low titer ($\frac{1}{40}$) in the immunofluorescent antibody assay for HIV-1 but gave ambiguous results in the HIV-1 Western blot assay with clear bands at p33, P53/55 and p64 but very weak bands at p24, gp41 and gp120. The woman had elevated serum IgG and IgM levels and a CD4/CD8 ratio of 0.46. Virus was isolated by co-cultivation of the woman's lymphocytes with PHA-stimulated lymphocytes from healthy uninfected donors. After 52 days in culture, virus was detected in the culture as judged by the presence of syncytia and on the basis of positive immunofluorescence observed when a laboratory reference anti-HIV antiserum was incubated with acetone-fixed cells from the culture. The presence of reverse transcriptase was also detected in the culture supernatant ($10^4$ cpm/ml, 27×background). Cell-free culture supernatant was used to passage the virus on fresh lymphocytes. After 15 days, CPE was again observed and reverse transcriptase detected in the supernatant. A comparison of detergent-treated culture supernatant from this isolate (ANT 70) with other isolates by differential antigen capturing revealed, however, that this isolate was not HIV-1.

These results are illustrated in FIG. 2. It is evident by the lower O.D. values that the isolate (ANT 70) is, in contrast to the other isolates, poorly recognized by the HIV-1 specific IgG but, like the other isolates, was readily captured by the broad specificity IgG (panel F). The other isolates, which were subsequently all shown to be HIV-1 strains using an HIV-1 specific MAb (CLB MAb 14), all gave higher O.D. values on the plates coated with specific IgG than on plates coated with the broad specificity reference IgG.

An attempt was made to transfer the virus to a permanent cell line by co-cultivating isolate (ANT 70)-infected primary lymphocytes with Molt-4 clone 8 cells. In the initial phase of the infection, extensive cytopathic effect was observed with syncytium formation and cell death. Within several weeks, cell growth was detected. The cells gave a positive immunofluorescence when tested using a broad spectrum anti-HIV antiserum and the presence of antigen and reverse transcriptase was easily detectable in the culture supernatant.

Virus was similarly isolated from the partner of the woman from whom isolate (ANT 70) was isolated (strain ANT 70 NA). The man was suffering from lymphadenopathy and was classified as class 3 according to the CDC classification system. The man also had elevated serum IgM and IgG levels and a CD4/CD8 ratio of 0.4. Virus was detected in the supernatant of the culture on day 18. Detergent-treated supernatant containing this virus was also analyzed by differential antigen capturing and found to react in a manner similar to isolate (ANT 70) (FIG. 3). The binding of antigen derived from this isolate was again less with HIV-1 specific IgG than with the broad specificity IgG.

Figure 4B:
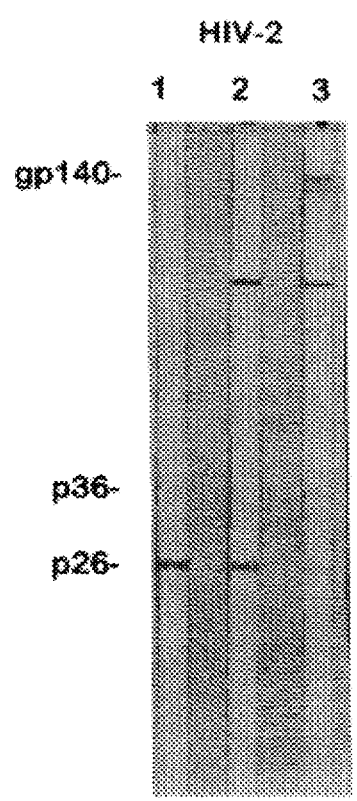

Serum from the person from whom the isolate (ANT 70 NA) was derived was incubated with HIV-1 and HIV-2 Western blot strips (Biotech). Additional strips were also incubated with serum from a donor infected with HIV-1 as well as serum from the person from whom HIV-2 (isolate 53) was isolated. These results are shown in FIG. 4. Serum from the person infected with ANT 70 NA crossreacted to a significant extent with virtually all HIV-1 proteins, including the envelope proteins. In contrast, serum from the HIV-2-infected individual crossreacted only with the gag p24 protein, p34 endonuclease and p68 reverse transcriptase. The anti-HIV-1 serum recognized only the p26 gag protein of HIV-2, while serum from the carrier of ANT 70 NA recognizes this protein and the HIV-2 reverse transcriptase.
Characterization of viral proteins Virus in the culture supernatant was precipitated using polyethylene glycol 6000 (Merck) and the resulting material was redissolved and pelleted through a 15 percent sucrose cushion. The pelleted virus was dissociated in SDS-sample buffer and analyzed by polyacrylamide gel electrophoresis followed by protein blotting. The blot, shown in FIG. 5, was incubated with a broad specificity anti-HIV serum to reveal the viral proteins.

Figure 6:
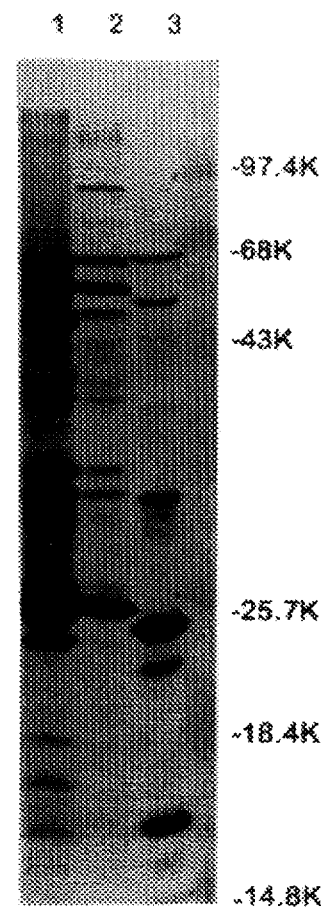

In addition to reacting with all of the HIV-1 viral proteins, the BSR antiserum also crossreacts with the gag and pol gene products of HIV-2. This antiserum clearly recognizes the gag and pol gene products of ANT 70 as well. It is evident that the molecular weights of the ANT 70 gene products differ from those of either HIV-1 or HIV-2. The molecular weights of the various viral proteins are summarized in table 1. The variability in the HIV-1 p17/p18 protein is due to a 6 amino acid insertion which is present in some strains between positions 120 and 121 in the HIV-1 HXB2 sequence. A comparison of the proteins from ANT 70 and ANT 70 NA are shown in FIG. 6. The molecular weights of all of the proteins of ANT 70 NA are identical to those of ANT 70.

In order to investigate further the antigenic relationship between HIV-1, HIV-2 and ANT 70, a series of African and European anti- HIV-1 sera were diluted 1:1000 and used to coat microwell plates for antigen capturing.

Figure 7:
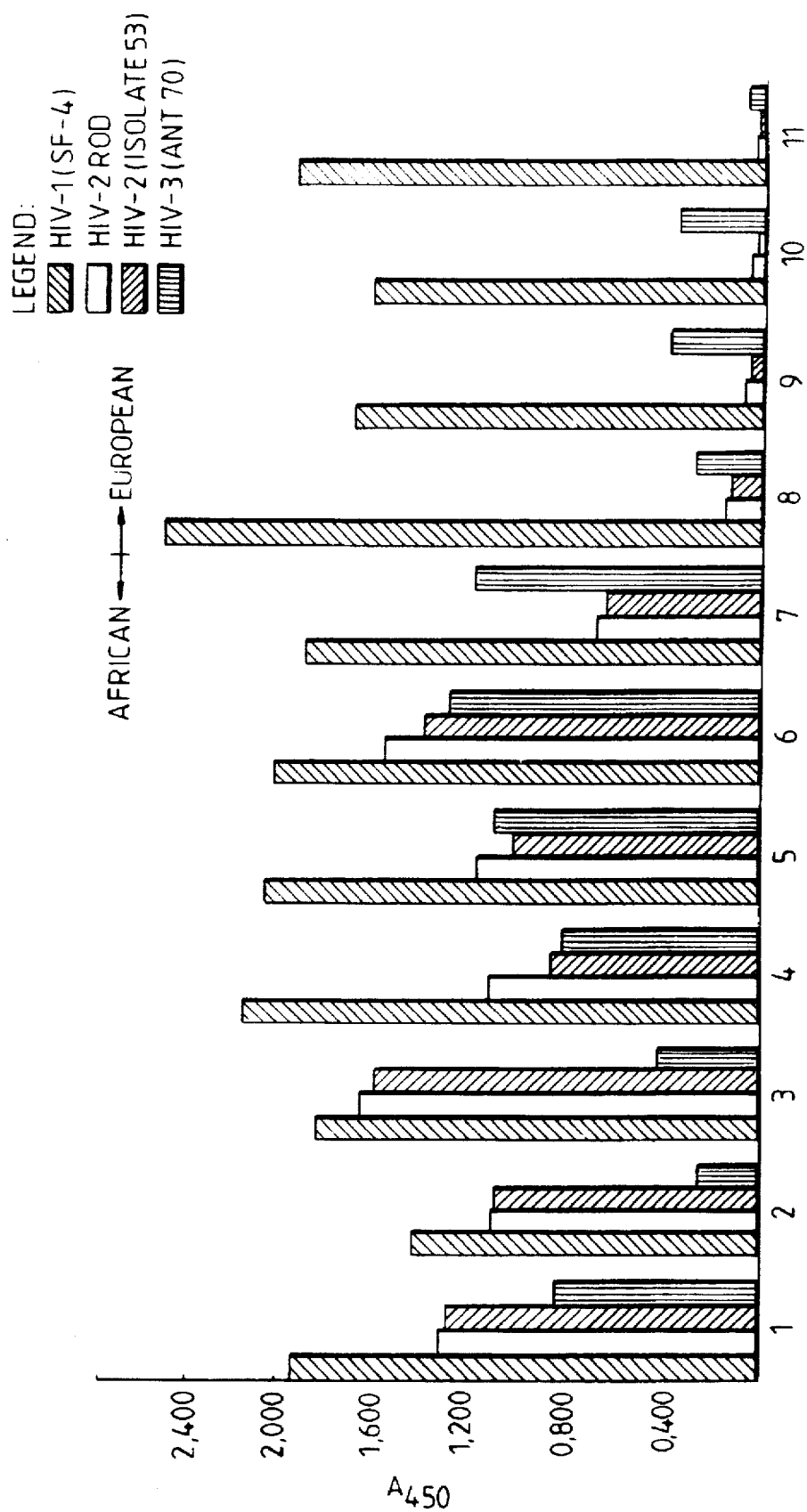

Detergent-treated culture supernatant containing HIV-1, ANT 70, HIV-2 (LAV-2rod) and HIV-2 (isolate 53) were diluted and the ability of each antiserum to capture the four different isolates was analyzed. Representative results are shown in FIG. 7. It can be seen from this experiment that the ability of the various sera to capture HIV-1 is in no way related to their ability to capture either HIV-2 or ANT 70. In contrast, the ability of these sera to capture LAV-2rod, the prototype HIV-2 strain, is strongly correlated with the ability of these sera to capture isolate 53, which is also an HIV-2 strain but an independent isolate. These data indicate that ANT 70 is neither HIV-1 nor HIV-2.

In a series of related antigen capturing experiments, four African anti-HIV-1 sera were chosen in order to access their ability to bind HIV-1, ANT 70, HIV-2 (LAV-2rod) and HIV-2 (isolate 53) when the IgGs were coated at different dilutions. Culture supernatants were diluted so as to give approximately the same optical density, when captured on plates coated with the IgG used in panel B of FIG. 8. Dilutions of the four sera were coated and virus- containing supernatant was added. The assumption was made that similar viruses should give rise to similar titration curves. Indeed, in FIG. 5, LAV-2rod and isolate 53 both react similarly with the coated IgGs. On the other hand, ANT 70 gave more intense signals at higher IgG dilutions than did either of the HIV-2 isolates and the shapes of the curves obtained with ANT 70 resemble more closely the curves obtained for HIV-1, except that the optical densities are consistently lower.

Figure 9:
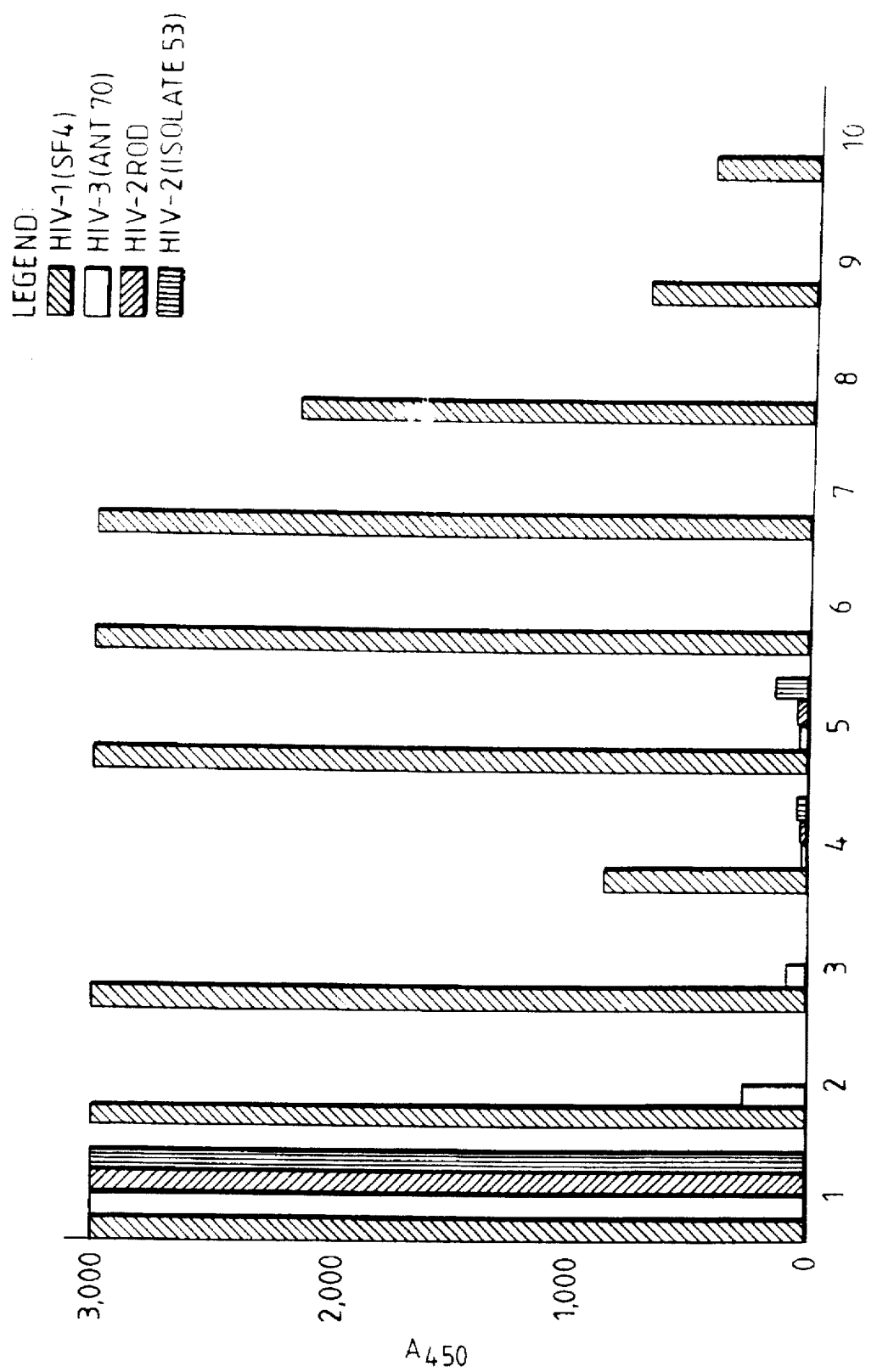
Figure 10A:
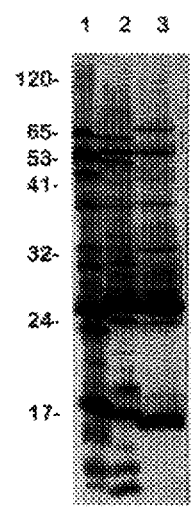
Figure 10B:
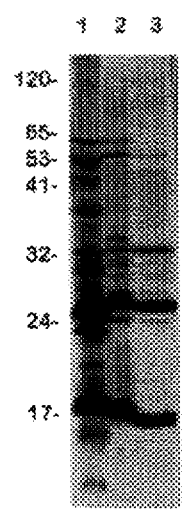
Figure 10C:
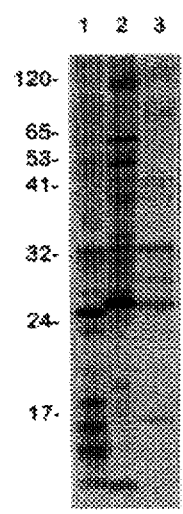
Figure 10D:
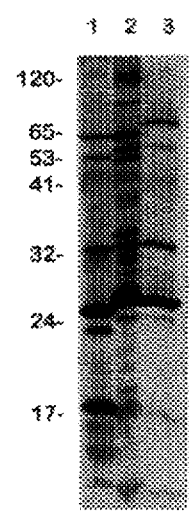
Figure 10E:

Cross reactivity of mouse monoclonal antibodies directed against HIV-1 p24 core protein A panel of mouse monoclonal antibodies (MAbs) prepared against the HIV-1 p24 core protein was tested for their ability to crossreact with ANT 70 and HIV-2 isolates. In principle, any panel of anti-HIV-1 p24 monoclonal antibodies can be used, as long as the series includes monoclonal antibodies which react with different epitopes on the HIV-1 p24 molecule. Ascites fluid containing the antibodies was diluted and used to coat microwell plates. Detergent-treated, virus-containing supernatants were then added to the coated wells. Bound antigen was detected using BSR-HIV IgGs conjugated to horseradish peroxidase. The results obtained are shown in FIG. 9.

In control wells coated with polyclonal broad spectrum IgGs, all virus-containing supernatants gave optical densities which exceeded the limits of the microwell plate reader. However, when tested in wells coated with the various monoclonal antibodies, quite a different pattern emerged. Previous studies indicated that all of the MAbs tested react against different epitopes on the p24 molecule with the exception of MAbs CLB 59 and CLB 21 which have been shown to recognize the same epitope. Both of these two MAbs react strongly with HIV-1 as expected and also give a measurable signal with ANT 70 but fail to react with either of the HIV-2 strains. Two other MAbs, CLB 64 and CLB 14, bound HIV-1 well and showed a weak affinity for ANT 70 as well as the two HIV-2 isolates. In particular, MAb CLB 14 has been shown to recognize all HIV-1 isolates well (>150 tested). This MAb must therefore bind to a very highly conserved epitope, remnants of which can also be detected in other human immunodeficiency viruses. The other MAbs to p24 (CLB 16, 47 and 19.7) and two others which were raised against the HIV-1 p18 protein (CLB 13.4 and CLB 13.6), f recognize either ANT 70 or the two HIV-2 isolates but did capture the corresponding HIV-1 antigens.
Reaction of human anti-HIV antisera to viral proteins.
Protein blots of viral proteins from HIV-1 (ARV 4), ANT 70 and HIV-2 (LAV2rod) were prepared after electrophoresis of detergent-solubilized extracts and incubated with various human sera (FIG. 10). Panel A shows the reaction of the broad specificity laboratory reference serum with the three virus isolates. In panel B, an anti-HIV-1 antiserum was incubated with the blot and recognizes preferentially HIV-1 proteins. Serum from the woman from whom ANT 70 was isolated (panel C) and her partner from whom ANT 70 NA was isolated (panel D) were tested for their ability to recognize other viral isolates. Both of these sera preferentially recognize ANT 70 including the gp120 envelope protein of this virus. Serum from the partner has a higher titer than serum from the woman from whom ANT 70 was isolated and recognizes the gp41 of HIV-1. Both of these sera have a higher affinity for ANT 70 than for HIV-1 or the HIV-2 isolates. In contrast, serum from the person from whom HIV-2 isolate 53 was isolated binds preferentially to HIV-2 proteins and recognizes the HIV-2 gp120 envelope protein of this virus as well as the gp41 transmembrane protein (panel E). It does not react with glycoproteins of HIV-1 or ANT 70. These results further indicate that ANT 70 is different from either HIV-1 or HIV-2.

Figure 11C:
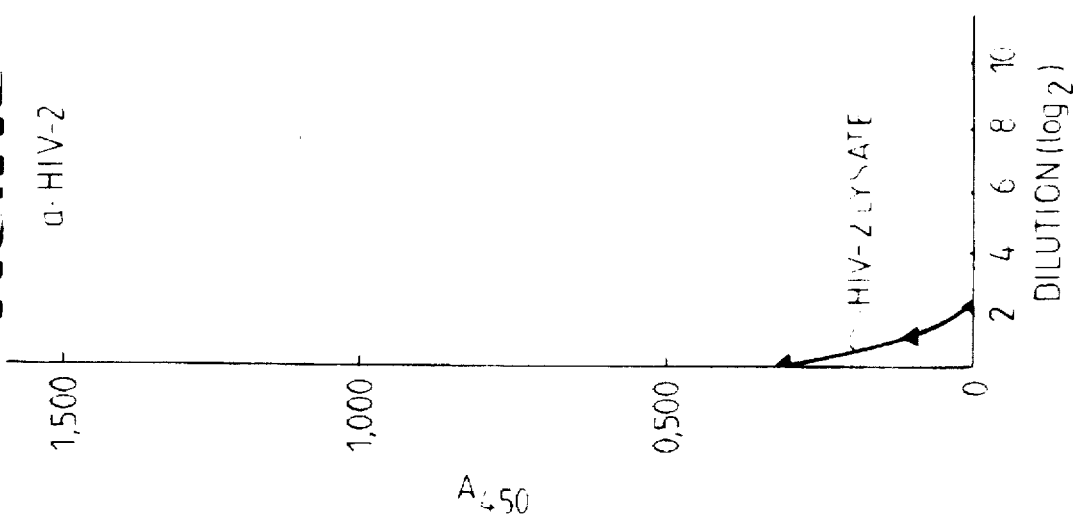
Figure 11B:
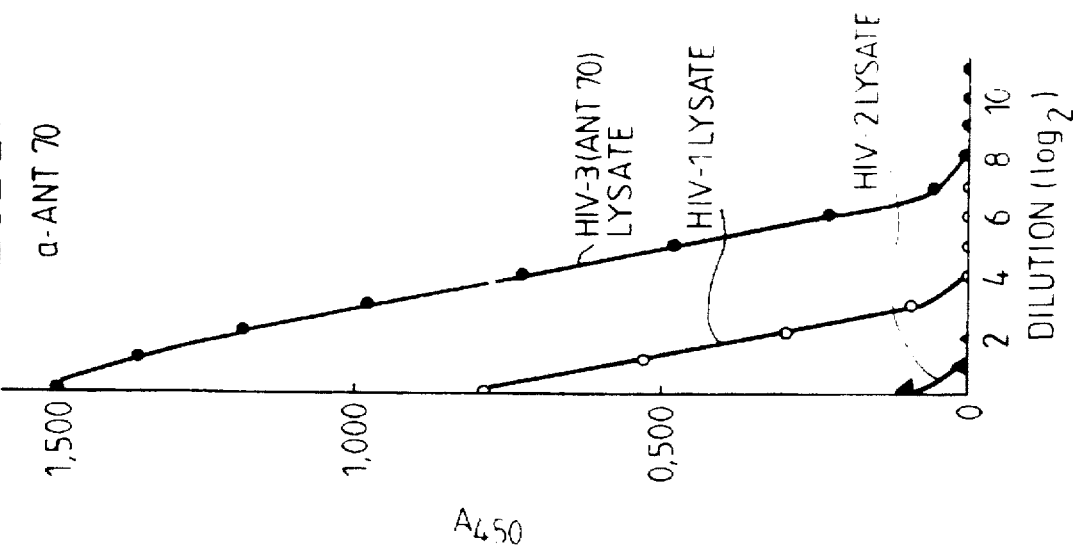
Figure 11A:
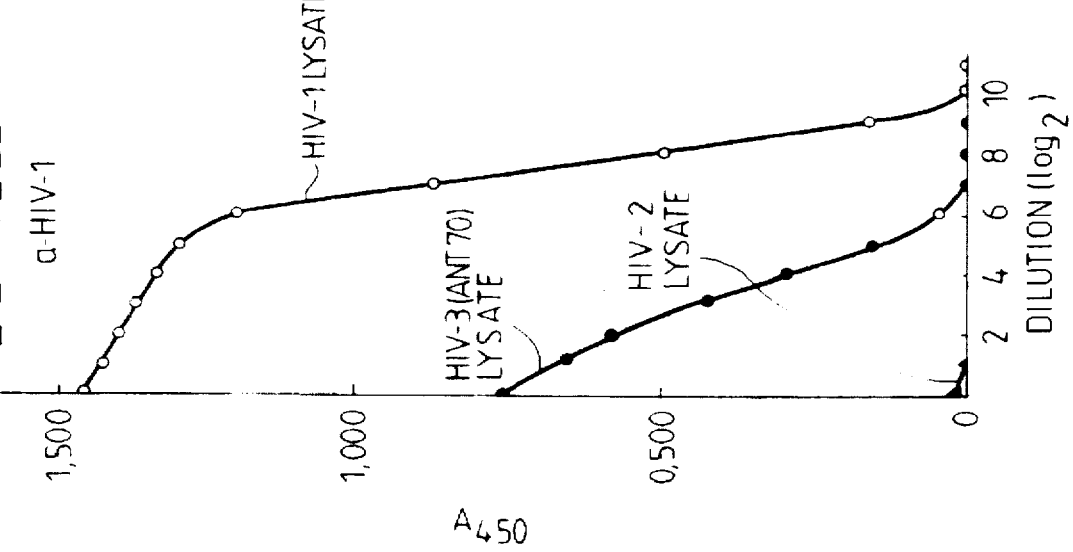

Enzyme immunosorbent assays using coated viral proteins titrations of anti-HIV-1, anti-ANT 70 and anti-HIV-2 sera were performed in microwell plates coated with HIV-1 (ARV-4), ANT 70 and HIV-2 (isolate 53) viral lysates. Two-fold dilutions of each sera, beginning at an initial dilution of 1:100, were tested for their ability to bind to the coated antigen. Bound antibody was detected using a horseradish peroxidase-labeled goat anti-human IgG conjugate. These results are shown in FIG. 11. The anti-HIV-1 serum recognized preferentially the HIV-1 proteins but shows a significant amount of crossreaction with ANT 70 proteins. The HIV-2 proteins were barely detected. In contrast, anti-ANT 70 serum preferentially recognized ANT 70 proteins, showed crossreactivity toward HIV-1 proteins, and reacted better with the HIV-2 coated wells than did the anti-HIV-1 serum as evidenced by the higher optical density values obtained. The anti-HIV-2 serum had a very low titer but nevertheless reacted best with HIV-2 proteins. No detectable signal was observed on HIV-1 or ANT 70 coated wells. The inability to detect crossreaction in this instance is undoubtedly related to the low anti-HIV titer of this serum.

Analysis of partial chemical cleavage products of viral proteins

The two reagents used for chemical cleavage, cyanogen bromide and BNPS-skatole, were chosen because of their high specificities for methionone (29) and tryptophan (30), respectively. These two amino acids are also rather hydrophobic and are therefore also less likely to found located in epitopes on the outer surfaces of protein molecules (31). Examination of published amino sequences of the gag and pol gene products of HIV-1 (32–36), HIV-2 (19), SIVagm (10), SIVmac (9), equine infectious anemia virus (EIAV,37) and Visna (38) reveals that while there is little amino acid homology between some of these diverse isolates, many of the positions of the methionine residues in these proteins and, to an even greater extent, the tryptophan residues, are strikingly conserved (FIG. 12). Futhermore, intraspecies variation in these residues is minimal or absent, at least in the case of HIV-1 (36) and probably holds true for all of the human and simian immunodeficiency retroviruses.

The partial digestion patterns of the gag and pol gene products of HIV-1, ANT 70, HIV-2 (LAVrod) and HIV-2 (isolate 53) are shown in FIG. 13.

Inspection of the CNBr cleavage patterns of the p24 protein from the four isolates reveals that the patterns generated for HIV-2 (LAV-2rod) and HIV-2 (isolate 53) are identical. Different patterns, however, are observed for HIV-1 and for ANT 70. Thus, significant differences exist in the locations of the methionine residues in the major core protein of HIV-1, ANT 70 and HIV-2. In the case of the p17 core protein, differences are observed between the two HIV-2 isolates. Inspection of the published sequence for HIV-2rod indicates that there is a methionine located 18 amino acids from the carboxyl terminus of this protein. We conclude that this methionine must be absent in the corresponding protein from isolate 53. From the cleavage pattern it is also possible to deduce the presence of a methionine near (10–15 amino acids) one of the termini of the p16 from ANT 70. CNBr cleavage of the retroviral reverse transcriptase reveals that again, the proteins from the two HIV-2 isolates are identical, while different patterns are observed for both HIV-1 and ANT 70 proteins. In the case of the p31 endonuclease derived from the 3'-portion of the pol gene, similarities can be deduced between all of the isolates although some minor differences are apparent.

BNPS-skatole cleavage of the p24 proteins from the four isolates results in strikingly similar patterns. It is evident from FIG. 8 that this is to be expected since the tryptophan positions in this protein are very highly conserved, particularly for the retroviruses of human and simian origin. We conclude that the tryptophan positions in the ANT 70 p25 protein also conform to this pattern. Inspection of the patterns reveals, however, that minor differences can be observed, not in the overall appearance of the pattern but rather in the apparent molecular weights of the species generalized by cleavage. In particular, differences are detected in the apparent molecular weights of the central spots in each pattern. As expected, the patterns for HIV-2 (LAV-2rod) and HIV-2 (isolate 53) are identical. The central spot in the pattern for ANT 70 has however, a larger apparent molecular weight while the central spot for HIV-1 (ARV-4) has a lower molecular weight. In regard to the p16, the positions of the tryptophans in the ANT 70 protein appear to resemble more closely the positions of the tryptophans found in the HIV-2 protein. The HIV-1 p17 has a tryptophan located 16 amino acids from the amino terminus of the protein and gives rise to an additional spot not seen in the ANT 70 and HIV-2 patterns following BNPS-skatole cleavage. The tryptophan corresponding to the one at position 36 in the HIV-1 p17 sequence is conserved in all isolates.

The patterns generated by cleavage of the reverse transcriptase from the four isolates are complex but is is once again apparent that the two HIV-2 isolates are identical. Patterns are obtained for ANT 70 which corresponds neither to the pattern obtained for HIV-1 nor to the HIV-2 pattern. Differences in apparent molecular weights of the cleavage products of the p31 endonuclease are also observed but the patterns generated from the corresponding proteins from HIV-1, ANT 70, and HIV-2 also show common features which suggests a conserved structure.

Results

Viral Nucleic Acids a. Hybridization of HIV-1 and HIV-2 cDNA to viral RNAs

Nucleicacids crosshybridization between HIV-1 and RNA from the viruses HIV-2 and ANT 70 was evaluated by performing the hybridization with the SacI-BglII HIV-1 restriction fragment which had been inserted into the vector pUC13. This fragment contains a portion of the 5' LTR, including the R region, the entire gag gene and most of the pol gene of HIV-1. Under stringent hybridization conditions, hybridization was only observed between this probe and the RNA derived from HIV-1 (SF4). No hybridization was observed between the probe and either HIV-2 or ANT 70 (FIG. 14). This indicates that the gag and pol regions of HIV-2 and ANT 70 are significantly different from the corresponding region of HIV-1.

The HIV-2 probe used contains a sequence of approximately 1000 base pairs derived from the env gene of HIV-2.

This probe hybridized only to HIV-2 RNA under stringent hybridization conditions and no hybridization was observed with either HIV-1 or HIV-3.

b. Homology between ANT 70 CDNA and sequences of HIV-1 and HIV-2

The CDNA cloneiso 70-11 was used as a probe to assess the degree of nucleic acid homology between the various virus isolates. The filter onto which aliquots of HIV-1, HIV-2 and ANT 70 had been deposited was subjected to hybridization under stringent conditions. The results are also shown in FIG. 14. The experiment demonstrates that under stringent hybridization conditions, no crosshybridization can be detected between any of the virus isolates. The ANT 70 derived probe hybridizes only to ANT 70.

c. Sequence analysis of clone iso 70-11

Subclones of the insert were made in pUC13 and sequenced using the dideoxynucleotide method:

The presence of a poly A tail confirmed that the iso 70-11 insert is derived from the 3' end of the viral RNA. Adjacent to the poly A tail is the sequence corresponding to the R region of the viral 3' LTR. Sequence contained in the ANT 70 cDNA and the viral sequences to which they correspond are shown below:

1. HIV-3 LTR

```
        10          20          30          40          50          60
CCCATGGATT  TGAAGATACA  CATAAAGAAA  TACTGATGTG  GAAGTTTGAT  AGATCTCTAG 70          80          90         100         110         120
GCAACACCCA  TGTTGCTATG  ATAACTCACC  CAGAGCTCTT  CCAGAAGGAC  TAAAAACTGC 130         140         150         160         170         180
TGACCTGAAG  ATTGCTGACA  CTGTGGAACT  TTCCAGCAAA  GACTGCTGAC  ACTGCGGGGA 190         200         210         220         230         240
CTTTCCAGTG  GGAGGGACAG  GGGGCGGTTC  GGGGAGTGGC  TAACCCTCAG  AAGCTGCATA 250         260         270         280         290         300
TAAGCAGCCG  CTTTCTGCTT  GTACCGGGTC  TCGGTTAGAG  GACCAGGTCT  GAGCCCGGGA
                 U3               R 310         320         330         340         350         360
GCTCCCTGGC  CTCTAGCTGA  ACCCGCTCGT  TAACGCTCAA  TAAAGCTTGC  CTTGAGTGAG
                                              Polyadenylation signal
```

A - POLY A

2. Sequences from HIV-3 3'ORF

```
        10          20          30          40          50          60
AACATGGGAAACGCATTGAGAAAAGGTAAATTTGAGGGATGGGCAGCAGTAAGAGAAAGA
Asn Met Gly Asn Ala Leu Arg Lys Gly Lys Phe Glu Gly Trp Ala Ala Val Arg Glu Arg 70          80          90         100         110         120
ATGAGAAGAACTAGAACTTTCCCTGAGTCTGAACCATGCGCACCTGGAGTAGGACAGATC
Met Arg Arg Thr Arg Thr Phe Pro Glu Ser Glu Pro Cys Ala Pro Gly Val Gly Gln Ile 130         140         150         160         170         180
TCCAGGGAATTAGCAGCTAGAGGAGGGATACCAAGTTCCCATACTCCTCAAAACAATGCA
Ser Arg Glu Leu Ala Ala Arg Gly Gly Ile Pro Ser Ser His Thr Pro Gln Asn Asn Ala 190         200         210         220         230         240
GCCCTTGCATTCCTAGAAAGTCACCAAGAGGAAGAAGTAGGTTTTCCAGTAGCACCTCAA
Ala Leu Ala Phe Leu Glu Ser His Gln Glu Glu Glu Val Gly Phe Pro Val Ala Pro Gln 250         260         270         280         290         300
GTGCCTCTAAGGCCAATGACCTATAAAGGAGCATTTGACCTCAGCTTCTTTTTAAAAGAA
Val Pro Leu Arg Pro Met Thr Tyr Lys Gly Ala Phe Asp Leu Ser Phe Phe Leu Lys Glu 310         320         330         340         350         360
AAGGGAGGACTGGAAGGGTTAATTTACTCCCATAAAAGAGCAGAAATCCTGGATCTTTGG
Lys Gly Gly Leu Glu Gly Leu Ile Tyr Ser His Lys Arg Ala Glu Ile Leu Asp Leu Trp

GTGTATAA
ValTyr
```

Discussion

We have isolated a novel human immunodeficiency-associated retrovirus from a Camerounian woman (ANT 70) and her partner (ANT 70 NA). At the time the original virus isolation was performed, the woman was only slightly seropositive, gave ambiguous results in the western blot test and was clinically asymptomatic. Since that time, the woman has begun to develop some of the symptoms of AIDS-related complex (ARC). In contrast, her partner, from whom we were also able to isolate a virus with the same characteristics as the original isolate, was suffering from lymphadenopathy and has since developed other symptoms characteristic of AIDS. This novel isolate may therefore be considered to be a human immunodeficiency virus. The fact that this same virus could be isolated from sexual partners also suggests a mode of transmission which is similar to that of human retroviruses.

The virus was first recognized as being different from HIV-1 on the basis of its altered ability to be captured in a differential antigen capturing assay. This has proven to be a highly reliable test which is able to distinguish between HIV-1 and non-HIV-1 strains. That this isolate is not HIV-1 is borne out at the protein level by 1.) the differing molecular weights of the viral proteins, 2.) a different pattern of crossreactivity with anti-HIV-1 antiserum than HIV-1, 3.) a drastically reduced ability to be recognized by mouse monoclonal antibodies raised against HIV-1 p24 and p17 core proteins, 4.) preferential recognition of ANT 70 proteins over HIV-1 proteins by antisera from the virus carrier, and 5.) patterns of partial cleavage of four of the most highly conserved viral proteins which do not match the patterns obtained when HIV-1 proteins are subjected to the same treatment. Nevertheless, sera from the two individuals infected with this virus recognize the HIV-1 gp41 envelope protein. By the same criteria listed above, it is also clear that ANT 70 is not HIV-2. Indeed, the antigenic differences between ANT 70 and HIV-1 are smaller than those between HIV-2 and HIV-1. This is particularly evident from the results presented in FIGS. 8 and 10.

Additional compelling evidence that ANT 70 is a unique virus different from HIV-1 and HIV-2 comes from the partial peptide maps. We have shown that there are significant differences in the most highly conserved viral proteins. The two HIV-2 isolates which were used for comparison gave essentially identical cleavage patterns except in the case of CNBr cleavage of the p17 core protein. It should be noted, however, that the p17 core protein exhibits more variability than the p24 protein, at least in HIV-1 strains (34). Whether or not this also holds true for HIV-2 awaits sequence determination on more strains than have been analyzed to date.

In light of the fact that ANT 70 is antigenically more closely related to HIV-1 than is HIV-2, as evidenced by a higher degree of crossreactivity which extends even to the gp41 envelope protein, it was essential to establish that ANT 70 was more than simply a genetic variant of HIV-1. This was possible by investigating the locations of some of the most highly conserved amino acids in a number of viral proteins which are least subject to genetic variation. That major differences were noted in the cleavage patterns indicates that HIV-1, HIV-2 and ANT 70 are three genetically distinct viruses. On the other hand, the same series of experiments also revealed similarities between the viruses which may indicate that all three arose from a common progenitor.

The hybridization data also support the notion that ANT 70 is fundamentally different from either HIV-1 and HIV-2. As long as the conditions under which the hybridization is performed are stringent, a distinction can easily be made between the three virus types. RNA of the HIV-3 retrovirus virtually hybridizes neither with the Env gene or the LTR close to it, in particular not with the nucleotide sequence 8352–9538 of HIV-1, nor with the sequences of the Pol region of the HIV-1 genome under stringent conditions.

Analysis of the cDNA sequences revealed that the insert is derived from the 3' end of the viral genome. An analysis of the homology between these sequences and the sequence of HIV-1 and HIV-2 reveal that ANT 70 is somewhat more closely related to HIV-1, particularly in the LTR sequences (approx. 70% homology). The differences are nevertheless of such magnitude as to rule out the possibility that ANT 70 is simply a genetic variant of HIV-1. The ANT 70 3' LTR also contains the signal sequences which are typical of retroviral LTRs.

The existence of a third type of human immunodeficiency virus has immediate epidemiological implications and consequences for blood bank testing. As has been shown, antibodies from people infected with this virus react preferentially with this virus, although these antibodies also crossreact with HIV-1 proteins. While it was possible to detect a positive reaction of ANT 70 NA serum in enzyme immunoassays, immunofluorescence assays and Western Blot assays based on HIV-1 proteins, the fact that the positive signal was due to a crossreaction inevitably implies that the sensitivity of such tests will be less for antibodies produced in response to this virus. This was amply demonstrated by the enzyme immunoassay results (FIG. 11). Furthermore, one criterion for seropositivity in the Western blot assay is the presence of detectable antibodies to both a gag and/or pol protein and one of the envelope proteins. Since in the case of the two individuals infected with ANT 70 and ANT 70 NA, respectively, crossreaction was observed to both HIV-1 p24 and the envelope proteins, the conclusion which is invariably drawn is that these individuals are infected with HIV-1 but for some reason fail to develop high titers against HIV-1. It is possible therefore, that this virus is more widespread than is currently realized. From an epidemiological standpoint, it is essential to develop specific diagnostic tests for this virus in order to evaluate the limits of the geographical area in Africa in which the virus can be found, and to evaluate the extent to which this virus has been disseminated.

REFERENCES

1. Dalgleish, A. G., Beverly, P. C. L., Clapham, P. R., Crawford, D. H., Greaves, M. F. and Weiss, R. A. (1984). The CD4 (T4) antigen is an essential component of the receptor for the AIDS retrovirus. *Nature* 312: 763–766.
2. Maddon, P. J., Dalgleish, A. G., McDougal, J. S., Clapham, P. R., Weiss, T. A. and Axel, R. (1986). The T4 gene encodes the AIDS virus receptor and is expressed in the immune system and the brain. *Cell* 47: 333–348.
3. Wong-Staal, F. and Gallo, R. C. (1985). Human T-lymphotropic retroviruses. *Nature* 317: 395–403.
4. Clavel, F., Guetard, D., Brun-Vezinet, F., Chamaret, S., Rey, M. A., Santos-Ferriera, M. D., Laurent, A. G., Dauguet, C., Katlama, C., Rouzioux, C., Klatzmann, D., Champalimaud, J. L. and Montagnier, L. (1986). Isolation of a new human retrovirus from West-African patients with AIDS. *Science* 233: 343–346.
5. Albert, J., Bredberg, U., Chiddi, F., Bottinger, B., Fenyo, E. M., Norrby, E. and Biberfeld, G. (1987). New pathogenic human retrovirus of West-African origin (SBL 6669) and its relationship to HTLV-IV, LAV-II and HTLV-IIIB. *AIDS Res.*
6. Kanki, P. J., Kurth, R., Becker, W., Dreesman, G., McLane, M. F. and Essex, M. Antibodies to simian T-lymphotropic virus type III in African green monkeys and recognition of STLV-III viral protein by AIDS and related sera. *Lancet* 1985, i: 1330–1332.
7. Kanki, P. J., Alroy, J. and Essex, M. (1985). Isolation of T-lymphotropic retrovirus related to HTLV-III/LAV from wild-caught African green monkeys. *Science* 230: 951–954.

8. Daniel, M. D., Letvin, N. L., King, N. W., Kannagi, M., Sehgal, P. K., Hunt, R. D., Kanki, P. J., Essex, M. and Desrosiers, R. C. (1985). Isolation of T-cell tropic HTLV-III-like retrovirus from macaques. *Science* 228: 1201–1204.

9. Chakrabarti, L., Guyader, M., Alizon, M., Daniel, M. D., Desrosiers, R. C., Tiollais, P., and Sonigo, P. (1987). Sequence of simian immunodeficiency virus from macaque and its relationship to other human and simian retroviruses. *Nature* 328: 543–547.

10. Franchini, G., Gurgo, C., Guo, H. -G., Gallo, R. C., Collati, E., Fargnoli, K. A., Hall, L. F., Wong-Staal, F. and Reitz, M. S. Jr. (1987). sequence of simian immunodeficiency virus and its relationship to the human immunodeficiency viruses. *Nature* 328: 539–543.

11. Benn, S., Rutledge, R., Folks, T., Gold, J., Baker, L., McCormick, J., Feorino, P., Piot, P., Quinn, T., and Martin, M. (1985) Genomic heterogeneity of AIDS retroviral isolates from North America and Zaire. *Science* 230: 949–951.

12. Hahn, B. H., Shaw, G. M., Taylor, M. E., Redfield, R. R., Markham, P. D., Salahuddin, S. Z., Wong-Staal, F., Gallo, R. C., Parks, E. S. and Parks, W. P. (1986). Genetic variation in HTLV-III/LAV over time in patients with AIDS or at risk for AIDS. *Science* 232: 1548–1553.

13. Magasiny, S., Spire, B., Barre-Sinoussi, F. and Chermann, J. -C. (1986). Genomic varaibility of selected LAV-related AIDS retroviruses. *AIDS Res.* 2: 19–30.

14. Alizon, M., Wain-Hobson, S., Motagnier, L. and Sonigo, P. (1985). Genetic variability of the AIDS virus: nucleotide sequence analysis of two isolates from African patients. *Cell* 46: 63–74.

15. Starcich, B. R., Hahn, B. H., Shaw, G. M., McNeely, P. D., Modrow, S., Wolf, H., Parks, E. S., Parks, W. P., Josephs, S. F., Gallo, R. C., Wong-Staal, F. (1986). Identification and characterization of conserved and variable regions in the envelope gene of HTLV-III/LAV, the retrovirus of AIDS. *Cell* 45: 637–648.

16. Willey, R. L., Rutledge, R. A., Dias, S., Folks, T., Theodore, T., Buckler, C. E. and MArtin, M. A. (1986). Identification of conserved and divergent domains within the envelope gene of the ecquired immunodeficiency syndrome retrovirus. *Proc. Matl. Acad. Sci. USA* 83: 5038–5042.

17. Clavel, F., Guyader, M., Guetard, D., Salle, M., Montagnier, L. and Alizon, M. (1986). Molecular cloning and polymorphism of the human immune deficiency virus type 2. *Nature* 324: 691–695.

18. Hahn, B. H., Kong, L. I., Lee, S. -W., Kumar, P., Taylor, M. E., Arya, S. K. and Shaw, G. M. (1987). Relationship of HTLV-4 to simian and human immunodeficiency-associated viruses. *Nature* 300: 184–186.

19. Guyader, M., Emerman, M., Sonigo, P., Clavel, F., Montagnier, L. and Alizon, M. (1987). Genome organization and transactivation of the human immunodeficiency virus type 2. *Nature* 326: 662–669.

20. Levy, J. A., Hoffman, A. D., Kramer, S. M., Landis, J. A., Shimabukuro, J. M. and Oshiro, L. S. (1984). Isolation of lymphocytopathic retroviruses from San Francisco patients with AIDS. *Science* 225: 840–842.

21. Vanderborght, B., De Leys, R. J., Van Heuverswyn, H., Merregaert, J., Prinsen, H., Nijs, P. Vercauteren, G., and van der Groen, G. (1988). Submitted for publication.

22. Levy, J. A. and Shimabukuro, J. (1985). Recovery of AIDS-associated retroviruses from patients with AIDS or AIDS-related conditions and from clinically healthy individuals. *J. Infect. Dis.* 152: 734–738.

23. van der Groen, G., Vercauteren, G. and Piot, P. (1987). Immunofluorescence tests for HIV antibody and their value as confirmatory tests. *J. Virol. Meth.* 17: 35–43.

24. Hoffman, A. D., Banapour, B. and Levy; J. A. (1985). Characterization of the AIDS-associated retrovirus reverse transcriptase and optimal conditions for its detection in virions. *Virology* 147: 326–335.

25. Kikukawa, R., Koyanagi, Y., Harada, S., Kobayashi, N., Hatanaka, M. and Yamamoto, N. (1986). Differential susceptibility to the acquired immunodeficiency syndrome retrovirus in cloned cells of human leukemic T-cell line Molt-4. *J. Virol.* 57: 1159–1162.

26. Winkel, I. N., Tersmette, M., Miedema, F. and Huisman, J. G. (1987). Identification of gag-epitopes by a panel of MAb in a series of HIV isolates. Abstracts of the Third International Conference on AIDS, Washington D.C., U.S.A., p. 116.

27. Maizel, J. V. (1971). Polyacrylamide gel electrophoresis of viral proteins; in *Methods in Virology*, Vol. 5, pp: 180–246, K. Maramorusch and H. Koprowski, Editor, Academic Press, New York, London.

28. Dunn, S. D. (1986) Effects of the modification of transfer buffer composition and the renaturation of proteins in gels on the recognition of proteins on Western blots by monoclonal antibodies. *Anal. Biochem.* 157: 144–153.

29. Gross, E. and Witkop, B. (1961). Selective cleavage of methionyl peptide bonds in RNAase with CNBr. *J. Am. Chem. Soc.* 83: 1511–1511.

30. Fontana, T. P. and Woods, K. R. (1981). Modification of tryptophanyl residues with BNPS-Skatole. *Meth. Enzymol.* 25/419–423.

31. Hopp, T. P. and Woods, K. R. (1981). Prediction of protein antigenic determinants from amino acid sequence. *Proc. Natl. Acad. Sci. USA* 78: 3824–3828.

32. Wain-Hobson, S., Sonigo, P., Danos, O., Cole, S. and Alizon, M. (1985). Nucleotide sequence of the AIDS virus, LAV. *Cell* 40: 9–17.

33. Ratner, L., Haseltine, W., Patarca, R., Livak, K. J., Starcich, B., Josephs, S. F., Doran, E. R., Rafalski, J. A., Whitehorn, E. A., Baumeister, K., Ivanoff, L., Petteway, S. R. Jr., Pearson, M. L., Lautenberger, J. A., Papas, T. S., Ghrayes, J., Chang, N. T., Gallo, R. C. and Wong-Staal, F. (1985). Complete nucleotide sequence of the AIDS virus, HTLV-III. *Nature* 313: 277–284.

34. Sanchez-Pescador, R., Power, M. D., Barr, P. J., Steimer, K. S., Stempien, M. M., Brown-Shimer, S. L., Gee, W. W., Renard, A., Randolph, A., Levy, J. A., Dina, D. and Luciw, P. (1985). Nucleotide sequence and expression of an AIDS-associated retrovirus (ARV-2) *Science* 227: 484–492.

35. Muesing, M. A., Smith, D. H., Cabradillo, C. D., Benton, C. V., Laskey, LA. A and Capon, D. J. (1985). Nucleic acid structure and expression of the human AIDS/lymphadenopathy retrovirus. *Nature* 313: 450–458.

36. Human retroviruses and AIDS. (1987). G. Meyers, A. B. Rabson, S. F. Josephs, T. F. Smith and F. Wong-Staal, Editors. Los Alamos National Laboratory, Los Alamos, N. Mex., U.S.A.

37. Kawakami, T., Sherman, L., Dahlberg, T., Gazit, A., Yaniv, A., Tronick, S. and Aarsonson, S. A. (1987). Nucleotide sequence analysis of Equine Infectious Anemia Virus proviral DNA. *Virology* 158: 300–312.

38. Sonigo, P., Alizon, M., Staskus, K., Klatzmann, D., Cole, S., Danos, O., Retzel, E., Tiollais, P., Haase, A. and Wain-Hobson, S. (1985). Nucleotide sequence of the Visna lentivirus: relationship to the AIDS virus. *Cell* 42: 369–382.

We claim:

1. A composition comprising at least one protein or glycoprotein of HIV-3 retrovirus, said retrovirus (also known as HIV-1 subtype O virus) having the morphological and immunological characteristics of any of the retroviruses deposited in the European Collection of Animal Cell Cultures under V88060301.

2. The composition of claim 1 wherein the composition comprises a total extract or lysate of HIV-3 retrovirus.

3. The composition of claim 1 wherein the composition comprises at least one of the internal core proteins of HIV-3 retrovirus selected from the group consisting of p12, p16 and p25.

4. The composition of claim 1 wherein the composition comprises at least one of the envelope glycoproteinsof HIV-3 retrovirus selected from the group consisting of gp41 and gp120.

5. A purified antigen of HIV-3 retrovirus (also known as HIV-1 subtype O virus) providing a single band in polyacrylamide gel electrophoresis, and containing an epitope that is immunoreactive with patient sera containing anti-HIV-3 antibodies.

6. A purified antigen selected from the group consisting of p12, p16, p25, gp41 and gp120, wherein the antigen is isolated from HIV-3 retrovirus (also known as HIV-1 subtype O virus).

7. The antigen of claim 6 wherein the antigen is the p12 protein of HIV-3, obtained by subjecting an extract or lysate of HIV-3 to gel electrophoresis and isolating the p12 protein from the gel.

8. The antigen of claim 6 wherein the antigen is the p16 protein of HIV-3, obtained by subjecting an extract or lysate of HIV-3 to gel electrophoresis and isolating the p16 protein from the gel.

9. The antigen of claim 6 wherein the antigen is the p25 protein of HIV-3, obtained by subjecting an extract or lysate of HIV-3 to gel electrophoresis and isolating the p25 protein from the gel.

10. The antigen of claim 6 wherein the antigen is the gp41 protein of HIV-3, obtained by subjecting an extract or lysate of HIV-3 to gel electrophoresis and isolating the gp41 protein from the gel.

11. The antigen of claim 6 wherein the antigen is the gp120 protein of HIV-3, obtained by subjecting an extract or lysate of HIV-3 to gel electrophoresis and isolating the gp120 protein from the gel.

12. A method for the production of antigens of HIV-3 retrovirus (also known as HIV-1 subtype O virus) comprising the steps of lysing the retrovirus and recovering the lysate containing HIV-3 antigens.

* * * * *